(12) United States Patent
Kawaue et al.

(10) Patent No.: US 8,227,169 B2
(45) Date of Patent: Jul. 24, 2012

(54) COMPOUND, ACID GENERATOR, RESIST COMPOSITION, AND METHOD OF FORMING RESIST PATTERN

(75) Inventors: Akiya Kawaue, Kawasaki (JP); Yoshiyuki Utsumi, Kawasaki (JP); Takehito Seo, Kawasaki (JP); Hideo Hada, Kawasaki (JP); Kotaro Endo, Kawasaki (JP); Daisuke Kawana, Kawasaki (JP); Yasuhiro Yoshii, Kawasaki (JP); Tsuyoshi Kurosawa, Kawasaki (JP)

(73) Assignee: Tokyo Ohka Kogyo Co., Ltd., Kanagawa (JP)

( * ) Notice: Subject to any disclaimer, the term of this patent is extended or adjusted under 35 U.S.C. 154(b) by 366 days.

(21) Appl. No.: 12/450,060

(22) PCT Filed: Apr. 4, 2008

(86) PCT No.: PCT/JP2008/056780
§ 371 (c)(1),
(2), (4) Date: Oct. 27, 2009

(87) PCT Pub. No.: WO2008/132966
PCT Pub. Date: Nov. 6, 2008

(65) Prior Publication Data
US 2010/0104973 A1 Apr. 29, 2010

(30) Foreign Application Priority Data

Apr. 17, 2007 (JP) ............................. P2007-108453
Jun. 6, 2007 (JP) ............................. P2007-150586
Oct. 23, 2007 (JP) ............................. P2007-275654

(51) Int. Cl.
*G03F 7/004* (2006.01)
*G03F 7/30* (2006.01)
*C07C 309/06* (2006.01)
(52) U.S. Cl. ................. 430/270.1; 430/326; 430/905; 430/910; 562/42; 562/113
(58) Field of Classification Search ........... 430/270.1, 430/326, 905, 910; 562/113, 42
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,624,328 B1 | 9/2003 | Guerra | |
| 7,074,543 B2 | 7/2006 | Iwai et al. | |
| 7,799,505 B2 * | 9/2010 | Kodama et al. | 430/270.1 |
| 2004/0087690 A1 * | 5/2004 | Lamanna et al. | 524/155 |
| 2005/0095532 A1 | 5/2005 | Kodama et al. | |
| 2010/0104973 A1 * | 4/2010 | Kawaue et al. | 430/270.1 |

FOREIGN PATENT DOCUMENTS

| | | |
|---|---|---|
| JP | 9-208554 | 8/1997 |
| JP | 11-035551 | 2/1999 |
| JP | 11-035552 | 2/1999 |
| JP | 11/035573 | 2/1999 |
| JP | 11-502543 | 3/1999 |
| JP | 11-322707 | 11/1999 |
| JP | 2003-241385 | 8/2003 |
| JP | 2005-099456 | 4/2005 |
| JP | 2005-099556 | 4/2005 |
| JP | 2005-122134 | 5/2005 |
| JP | 2006-504785 | 2/2006 |
| JP | 2006-348382 | 12/2006 |
| WO | 96/21953 | 7/1996 |
| WO | 2004/074242 | 9/2004 |

OTHER PUBLICATIONS

International Search Report issued Jun. 17, 2008 in International (PCT) Application No. PCT/JP2008/056780.

\* cited by examiner

*Primary Examiner* — John Chu
(74) *Attorney, Agent, or Firm* — Wenderoth, Lind & Ponack, L.L.P.

(57) ABSTRACT

There are provided a compound preferable as an acid generator for a resist composition, an acid generator including the compound, a resist composition containing the acid generator, and a method of forming a resist pattern using the resist composition, and the compound is represented by general formula (b1-12) shown below:

$$R^2—CH_2—O—Y^1—SO_3^-A^+ \quad (b1\text{-}12)$$

wherein $R^2$ represents a monovalent aromatic organic group; $Y^1$ represents an alkylene group of 1 to 4 carbon atoms which may be fluorinated; and $A^+$ represents a cation.

9 Claims, No Drawings

COMPOUND, ACID GENERATOR, RESIST COMPOSITION, AND METHOD OF FORMING RESIST PATTERN

This application is a U.S. national stage of International Application No. PCT/JP2008/056780 filed Apr. 4, 2008.

TECHNICAL FIELD

The present invention relates to a compound preferable as an acid generator for a resist composition, an acid generator including the compound, a resist composition containing the acid generator, and a method of forming a resist pattern using the resist composition.

Priority is claimed on Japanese Patent Application No. 2007-108453, filed Apr. 17, 2007, Japanese Patent Application No. 2007-150586, filed Jun. 6, 2007, and Japanese Patent Application No. 2007-275654, filed Oct. 23, 2007, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under the action of acid and an acid generator that generates acid upon exposure. For example, a chemically amplified positive resist contains, as a base resin, a resin which exhibits increased solubility in an alkali developing solution under the action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid dissociable, dissolution inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm.

As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

[Patent Document 1] Japanese Unexamined Patent Application, First Publication No. 2003-241385

DISCLOSURE OF INVENTION

Problems to be Solved by the Invention

As acid generators usable in a chemically amplified resist, various types have been proposed including, for example, onium salt-based acid generators such as iodonium salts and sulfonium salts. Currently, as the anion moiety for the aforementioned onium salt-based acid generators, a perfluoroalkylsulfonic acid ion is generally used. It is considered that the perfluoroalkyl chain within the anion moiety is preferably long, as diffusion of acid after exposure can be suppressed. However, a perfluoroalkyl chain of 6 to 10 carbon atoms is hardly decomposable, and hence, in consideration of safety in handling in terms of bioaccumulation, a nonafluorobutane-sulfonic acid ion or the like is used. Therefore, development of a novel compound which is more preferable as an acid generator for a resist composition has been demanded.

The present invention takes the above circumstances into consideration, with an object of providing a novel compound, an acid generator including the compound, a resist composition containing the acid generator, and a method of forming a resist pattern using the resist composition.

Means for Solving the Problems

In order to achieve the above object, a first aspect of the present invention is a compound represented by general formula (b1-12) shown below:

$$R^2-CH_2-O-Y^1-SO_3^-A^+ \quad \text{(b1-12)}$$

wherein $R^2$ represents a monovalent aromatic organic group; $Y^1$ represents an alkylene group of 1 to 4 carbon atoms which may be fluorinated; and $A^+$ represents a cation.

Moreover, a second aspect of the present invention is an acid generator including the compound according to the aforementioned first aspect.

Further, a third aspect of the present invention is a resist composition including a base component (A) which exhibits changed solubility in an alkali developing solution under the action of acid and an acid-generator component (B) which generates acid upon exposure, the acid-generator component (B) including an acid generator (B1) including a compound represented by general formula (b1-12) shown below:

$$R^2—CH_2—O—Y^1—SO_3^-A^+ \quad (b1\text{-}12)$$

wherein $R^2$ represents a monovalent aromatic organic group; $Y^1$ represents an alkylene group of 1 to 4 carbon atoms which may be fluorinated; and $A^+$ represents a cation.

Furthermore, a fourth aspect of the present invention is a method of forming a resist pattern, including: applying a resist composition of the aforementioned third aspect to a substrate to form a resist film on the substrate; conducting exposure of the resist film; and alkali-developing the resist film to form a resist pattern.

In the present description and claims, the term "structural unit" refers to a monomer unit that contributes to the formation of a resin component (polymer).

The term "exposure" is used as a general concept that includes irradiation with any form of radiation.

Effects of the Invention

According to the present invention, there are provided a novel compound preferable as an acid generator for a resist composition, an acid generator including the compound, a resist composition containing the acid generator, and a method of forming a resist pattern using the resist composition.

BEST MODE FOR CARRYING OUT THE INVENTION

As follows is a more detailed description of the present invention.

<<Compound>>

The compound according to the first aspect of the present invention is represented by general formula (b1-12) shown above.

In the aforementioned general formula (b1-12), $R^2$ represents a monovalent aromatic organic group; $Y^1$ represents an alkylene group of 1 to 4 carbon atoms which may be fluorinated; and $A^+$ represents a cation.

Examples of monovalent aromatic organic groups for $R^2$ include aryl groups in which one hydrogen atom has been removed from an aromatic hydrocarbon ring, such as a phenyl group, a biphenyl group, a fluorenyl group, a naphthyl group, an anthryl group, and a phenanthryl group; heteroaryl groups in which some of the carbon atoms constituting the ring(s) of these groups are substituted with hetero atoms such as an oxygen atom, a sulfur atom, and a nitrogen atom; and arylalkyl groups such as a benzyl group and a phenethyl group. In the above-mentioned arylalkyl groups, the alkyl chain preferably has 1 to 4 carbon atoms, more preferably 1 to 3 carbon atoms, and it is particularly desirable that the alkyl chain have 1 or 2 carbon atoms.

These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as the substituent preferably has 1 to 8 carbon atoms, and more preferably 1 to 4 carbon atoms. The halogenated alkyl group is preferably a fluorinated alkyl group. Examples of halogen atoms include a fluorine atom, a chlorine atom, an iodine atom and a bromine atom, and a fluorine atom is preferable.

The monovalent aromatic organic group for $R^2$ preferably has 6 to 20 carbon atoms, more preferably 6 to 10 carbon atoms, and most preferably 10 carbon atoms.

Examples of alkylene groups of 1 to 4 carbon atoms for $Y^1$ which may be fluorinated include $—CF_2—$, $—CF_2CF_2—$, $—CF_2CF_2CF_2—$, $—CF(CF_3)CF_2—$, $—CF(CF_2CF_3)—$, $—C(CF_3)_2—$, $—CF_2CF_2CF_2CF_2—$, $—CF(CF_3)CF_2CF_2—$, $—CF_2CF(CF_3)CF_2—$, $—CF(CF_3)CF(CF_3)—$, $—C(CF_3)_2CF_2—$, $—CF(CF_2CF_3)CF_2—$, $—CF(CF_2CF_2CF_3)—$, $—C(CF_3)(CF_2CF_3)—$; $—CHF—$, $—CH_2CF_2—$, $—CH_2CH_2CF_2—$, $—CH_2CF_2CF_2—$, $—CH(CF_3)CH_2—$, $—CH(CF_2CF_3)—$, $—C(CH_3)(CF_3)—$, $—CH_2CH_2CH_2CF_2—$, $—CH_2CH_2CF_2CF_2—$, $—CH(CF_3)CH_2CH_2—$, $—CH_2CH(CF_3)CH_2—$, $—CH(CF_3)CH(CF_3)—$, $—C(CF_3)_2CH_2—$; $—CH_2—$, $—CH_2CH_2—$, $—CH_2CH_2CH_2—$, $—CH(CH_3)CH_2—$, $—CH(CH_2CH_3)—$, $—C(CH_3)_2—$, $—CH_2CH_2CH_2CH_2—$, $—CH(CH_3)CH_2CH_2—$, $—CH_2CH(CH_3)CH_2—$, $—CH(CH_3)CH(CH_3)—$, $—C(CH_3)_2CH_2—$, $—CH(CH_2CH_3)CH_2—$, $—CH(CH_2CH_2CH_3)—$, and $—C(CH_3)(CH_2CH_3)—$.

As the alkylene group of 1 to 4 carbon atoms for $Y^1$ which may be fluorinated, it is preferable that the carbon atom bonded to S be fluorinated. Examples of such fluorinated alkylene groups include $—CF_2—$, $—CF_2CF_2—$, $—CF_2CF_2CF_2—$, $—CF(CF_3)CF_2—$, $—CF_2CF_2CF_2CF_2—$, $—CF(CF_3)CF_2CF_2—$, $—CF_2CF(CF_3)CF_2—$, $—CF(CF_3)CF(CF_3)—$, $—C(CF_3)_2CF_2—$, $—CF(CF_2CF_3)CF_2—$; $—CH_2CF_2—$, $—CH_2CH_2CF_2—$, $—CH_2CF_2CF_2—$; $—CH_2CH_2CH_2CF_2—$, $—CH_2CH_2CF_2CF_2—$, and $—CH_2CF_2CF_2CF_2—$.

Among these, $—CF_2CF_2—$, $—CF_2CF_2CF_2—$, and $CH_2CF_2CF_2—$ are preferable, $—CF_2CF_2—$ and $—CF_2CF_2CF_2—$ are more preferable, and $—CF_2CF_2—$ is particularly desirable.

As the cation for $A^+$, there is no particular limitation, and any of those conventionally known as a cation moiety for an onium salt-based acid generator can be appropriately selected for use. More specifically, a cation moiety represented by general formula (b'-1), (b'-2), (b-5) or (b-6) shown below can be preferably used.

[Chemical Formula 1]

wherein $R^{1'''}$ to $R^{3'''}$, $R^{5'''}$ and $R^{6'''}$ each independently represents an aryl group or an alkyl group, wherein two of $R^{1'''}$ to $R^{3'''}$ in general formula (b'-1) may be bonded to each other to form a ring with the sulfur atom in the formula; with the proviso that at least one of $R^{1'''}$ to $R^{3'''}$ represents an aryl group, and at least one of $R^{5'''}$ and $R^{6'''}$ represents an aryl group.

[Chemical Formula 2]

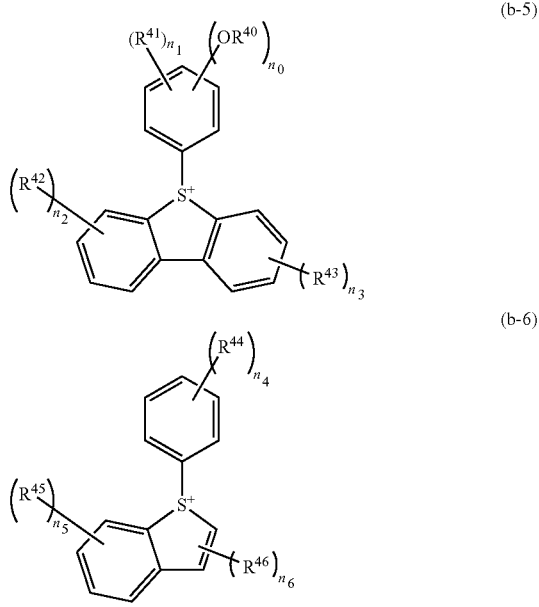

(b-5)

(b-6)

wherein $R^{40}$ represents a hydrogen atom, an alkyl group, an alkoxyalkyl group or an alkoxycarbonylalkyl group; $R^{41}$ represents an alkyl group, an acetyl group, a carboxyl group or a hydroxyalkyl group; each of $R^{42}$ to $R^{46}$ independently represents an alkyl group, an acetyl group, an alkoxy group, a carboxyl group or a hydroxyalkyl group; each of $n_0$ to $n_5$ independently represents an integer of 0 to 3, with the proviso that $n_0+n_1$ is 5 or less; and $n_6$ represents an integer of 0 to 2.

In general formula (b'-1), $R^{1'''}$ to $R^{3'''}$ each independently represents an aryl group or an alkyl group. Two of $R^{1'''}$ to $R^{3'''}$ in general formula (b'-1) may be bonded to each other to form a ring with the sulfur atom in the formula.

Further, among $R^{1'''}$ to $R^{3'''}$, at least one group represents an aryl group. Among $R^{1'''}$ to $R^{3'''}$, two or more groups are preferably aryl groups, and it is particularly desirable that all of $R^{1'''}$ to $R^{3'''}$ are aryl groups.

The aryl group for $R^{1'''}$ to $R^{3'''}$ is not particularly limited. Examples thereof include an unsubstituted aryl group having 6 to 20 carbon atoms, and a substituted aryl group in which a part or all of the hydrogen atoms of the aforementioned unsubstituted aryl group have been substituted with alkyl groups, alkoxy groups, alkoxyalkyloxy groups, alkoxycarbonylalkyloxy groups, alkoxycarbonyloxy groups, halogen atoms, hydroxyl groups or the like.

The unsubstituted aryl group is preferably an aryl group having 6 to 10 carbon atoms because it can be synthesized at a low cost. Specific examples thereof include a phenyl group and a naphthyl group.

The alkyl group as the substituent for the substituted aryl group is preferably an alkyl group having 1 to 5 carbon atoms, and most preferably a methyl group, an ethyl group, a propyl group, an n-butyl group, or a tert-butyl group.

The alkoxy group as the substituent for the substituted aryl group is preferably an alkoxy group having 1 to 5 carbon atoms, and most preferably a methoxy group, an ethoxy group, an n-propoxy group, an iso-propoxy group, an n-butoxy group or a tert-butoxy group.

The halogen atom as the substituent for the substituted aryl group is preferably a fluorine atom.

Examples of the alkoxyalkyloxy group as the substituent for the substituted aryl group include a group represented by a general formula: —O—C($R^{47}$)($R^{48}$)—O—$R^{49}$ [wherein each of $R^{47}$ and $R^{48}$ independently represents a hydrogen atom or a linear or branched alkyl group; and $R^{49}$ represents an alkyl group].

The alkyl group for $R^{47}$ and $R^{48}$ preferably has 1 to 5 carbon atoms, and may be either linear or branched, and is preferably an ethyl group or a methyl group, and most preferably a methyl group.

It is preferable that at least one of $R^{47}$ and $R^{48}$ be a hydrogen atom, and it is particularly desirable that either one of $R^{47}$ and $R^{48}$ be a hydrogen atom, and the other be a hydrogen atom or a methyl group, or both be hydrogen.

The alkyl group for $R^{49}$ preferably has 1 to 15 carbon atoms, and may be linear, branched or cyclic.

The linear or branched alkyl group for $R^{49}$ preferably has 1 to 5 carbon atoms.

Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of polycycloalkane include adamantane, norbornane, isobornane, tricyclodecane and tetracyclododecane. Of these, a group in which one or more hydrogen atoms have been removed from adamantane is preferable.

An example of the alkoxycarbonylalkyloxy group as the substituent for the substituted aryl group includes a group represented by a general formula: —O—$R^{50}$—C(=O)—O—$R^{51}$ [wherein $R^{50}$ represents a linear or branched alkylene group; and $R^{51}$ represents a tertiary alkyl group].

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

The tertiary alkyl group for $R^{51}$ preferably has 4 to 20 carbon atoms, and examples thereof include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

Examples of the alkoxycarbonyloxy group as the substituent for the substituted aryl group include a group represented by a general formula: —O—C(=O)—O—$R^{51}$ [wherein $R^{51}$ is as defined above]. Specific examples thereof include a tert-butyloxycarbonyloxy group and a tert-pentyloxycarbonyloxy group.

The alkyl group for $R^{1'''}$ to $R^{3'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

Of these, it is particularly desirable that each of $R^{1''}$ to $R^{3''}$ be a substituted or unsubstituted phenyl group or naphthyl group.

In terms of achieving excellent solubility in a resist solvent, inclusion of a substituted phenyl group having an alkoxy group or an alkoxycarbonylalkyloxy group as a substituent group is particularly preferred.

When two of $R^{1''}$ to $R^{3''}$ in general formula (b'-1) are bonded to each other to form a ring with the sulfur atom shown in the formula, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom. Furthermore, the above ring is preferably an aliphatic cyclic group.

When two of $R^{1''}$ to $R^{3''}$ in general formula (b'-1) are bonded to each other to form a ring with the sulfur atom shown in the formula, the remaining one of $R^{1''}$ to $R^{3''}$ is preferably an aryl group.

As examples of the aryl group, the same as the above-mentioned aryl groups for $R^{1''}$ to $R^{3''}$ can be exemplified.

Specific examples of a cation moiety represented by general formula (b'-1) include triphenylsulfonium, (3,5-dimethylphenyl)diphenylsulfonium, (4-(2-adamantoxymethyloxy)-3,5-dimethylphenyl)diphenylsulfonium, (4-(2-adamantoxymethyloxy)phenyl)diphenylsulfonium, (4-(tert-butoxycarbonylmethyloxy)phenyl)diphenylsulfonium, (4-(tert-butoxycarbonylmethyloxy)-3,5-dimethylphenyl)diphenylsulfonium, (4-(2-methyl-2-adamantyloxycarbonylmethyloxy)phenyl)diphenylsulfonium, (4-(2-methyl-2-adamantyloxycarbonylmethyloxy)-3,5-dimethylphenyl)diphenylsulfonium, tri(4-methylphenyl)sulfonium, dimethyl(4-hydroxynaphthyl)sulfonium, monophenyldimethylsulfonium, diphenylmonomethylsulfonium, (4-methylphenyl)diphenylsulfonium, (4-methoxyphenyl)diphenylsulfonium, tri(4-tert-butyl)phenylsulfonium, diphenyl(1-(4-methoxy)naphthyl)sulfonium, di(1-naphthyl)phenylsulfonium, 1-phenyltetrahydrothiophenium, 1-(4-methylphenyl)tetrahydrothiophenium, 1-(3,5-dimethyl-4-hydroxyphenyl)tetrahydrothiophenium, 1-(4-methoxynaphthalene-1-yl)tetrahydrothiophenium, 1-(4-ethoxynaphthalene-1-yl)tetrahydrothiophenium, 1-(4-n-butoxynaphthalene-1-yl)tetrahydrothiophenium, 1-phenyltetrahydrothiopyranium, 1-(4-hydroxyphenyl)tetrahydrothiopyranium, 1-(3,5-dimethyl-4-hydroxyphenyl)tetrahydrothiopyranium and 1-(4-methylphenyl)tetrahydrothiopyranium.

In general formula (b'-2), $R^{5''}$ and $R^{6''}$ each independently represents an aryl group or an alkyl group. At least one of $R^{5''}$ and $R^{6''}$ represents an aryl group. It is preferable that both of $R^{5''}$ and $R^{6''}$ represent an aryl group.

As the aryl group for $R^{5''}$ and $R^{6''}$, the same as the aryl groups for $R^{1''}$ to $R^{3''}$ can be exemplified.

As the alkyl group for $R^{5''}$ and $R^{6''}$, the same as the alkyl groups for $R^{1''}$ to $R^{3''}$ can be exemplified.

It is particularly desirable that both of $R^{5''}$ and $R^{6''}$ represent a phenyl group.

Specific examples of a cation moiety represented by general formula (b'-2) include diphenyliodonium and bis(4-tert-butylphenyl)iodonium.

In general formulas (b-5) and (b-6), with respect to $R^{40}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably an aforementioned alkyl group in which one or more hydrogen atoms have been substituted with hydroxy groups, and examples thereof include a hydroxymethyl group, a hydroxyethyl group and a hydroxypropyl group.

Examples of the alkoxyalkyl group for $R^{40}$ include groups that correspond to the alkoxyalkyl group within the alkoxyalkyloxy group exemplified above as "alkoxyalkyloxy group as the substituent for the substituted aryl group" (for example, a group represented by a general formula: —$C(R^{47})(R^{48})$—O—$R^{49}$ [wherein $R^{47}$, $R^{48}$ and $R^{49}$ are as defined above and specific examples thereof include the same as those mentioned above]).

Examples of the alkoxycarbonylalkyl group for $R^{40}$ include groups that correspond to the alkoxycarbonylalkyl group within the alkoxycarbonylalkyloxy group exemplified above as "alkoxycarbonylalkyloxy group as the substituent for the substituted aryl group" (for example, a group represented by a general formula: —$R^{50}$—$C(=O)$—O—$R^{51}$ [wherein $R^{50}$ and $R^{51}$ are as defined above]).

$n_0$ is preferably 0 or 1, and more preferably 0.

$n_1$ is preferably 0 to 2, more preferably 0 or 1, and still more preferably 0.

It is preferable that $n_2$ and $n_3$ each independently represents 0 or 1, and more preferably 0.

$n_4$ is preferably 0 to 2, and more preferably 0 or 1.

$n_5$ is preferably 0 or 1, and more preferably 0.

$n_6$ is preferably 0 or 1.

As the compound according to the first aspect of the present invention, compounds represented by formulas (b-12-1) to (b-12-36) shown below are preferred.

[Chemical Formula 3]

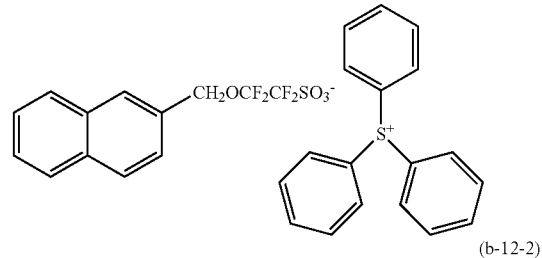

(b-12-1)

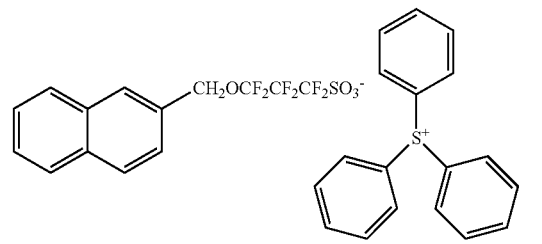

(b-12-2)

(b-12-3)
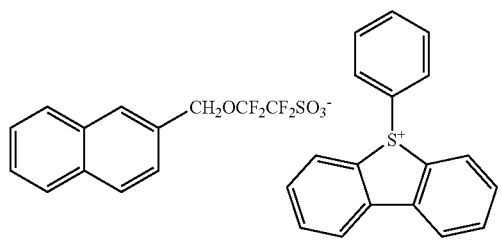
(b-12-4)
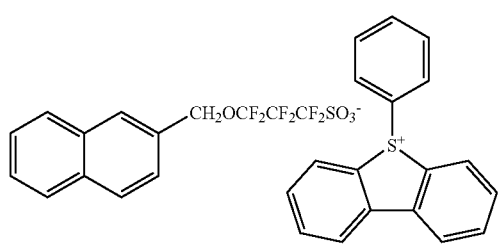
(b-12-5)
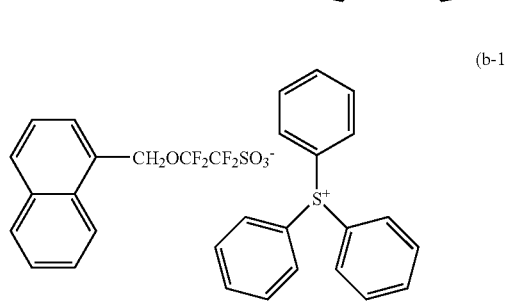
(b-12-6)
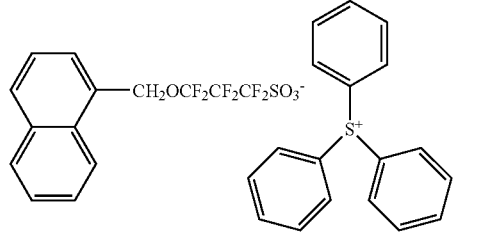
(b-12-7)
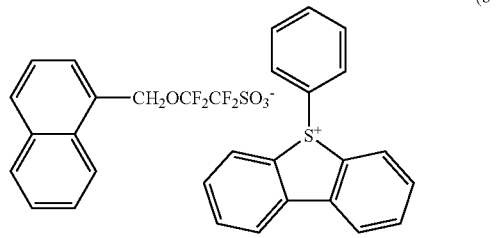
(b-12-8)
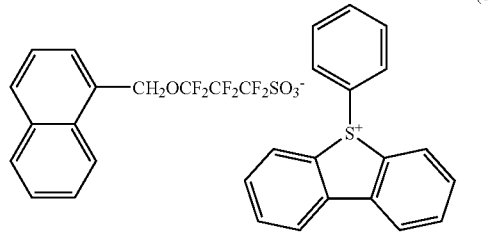
[Chemical Formula 4]
(b-12-9)
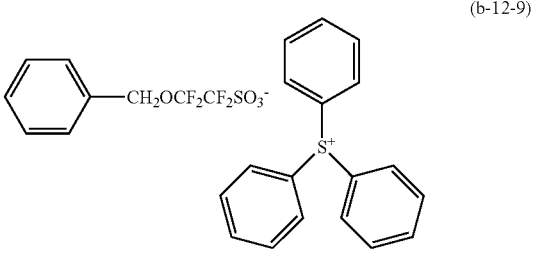
(b-12-10)
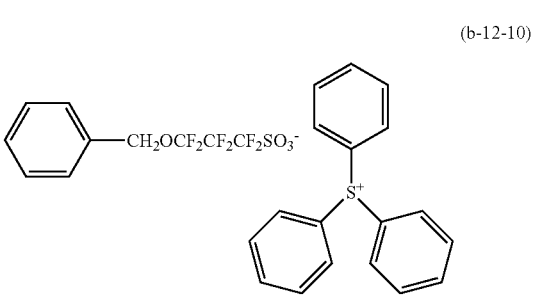
(b-12-11)
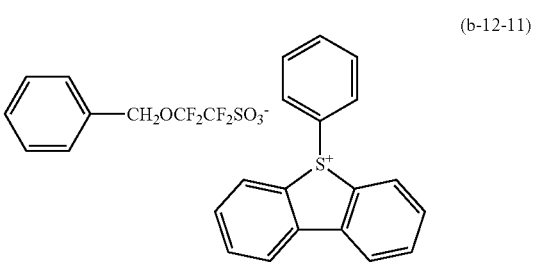
(b-12-12)
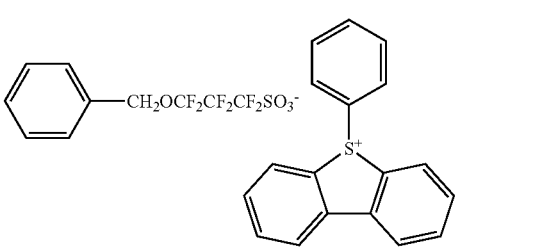
[Chemical Formula 5]
(b-12-13)
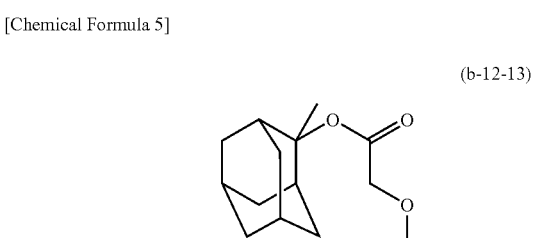

(b-12-14)
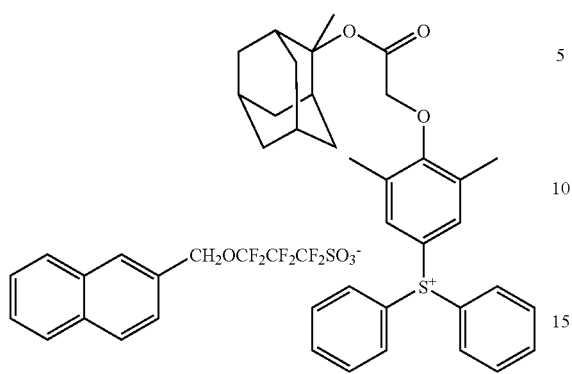
(b-12-15)
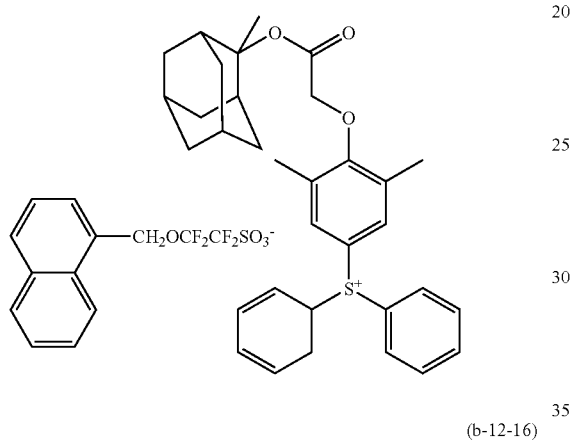
(b-12-16)
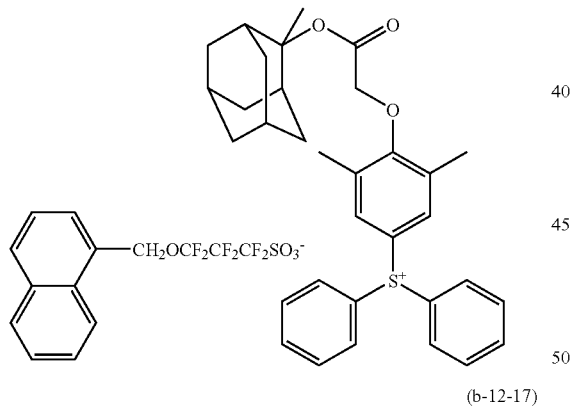
(b-12-17)
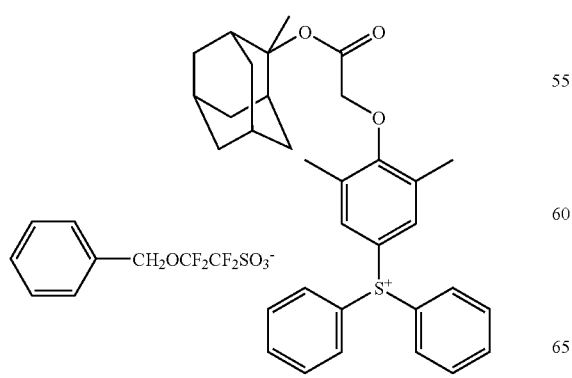
(b-12-18)
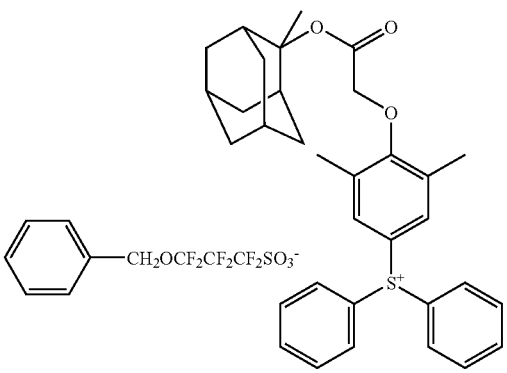
[Chemical Formula 6]
(b-12-19)
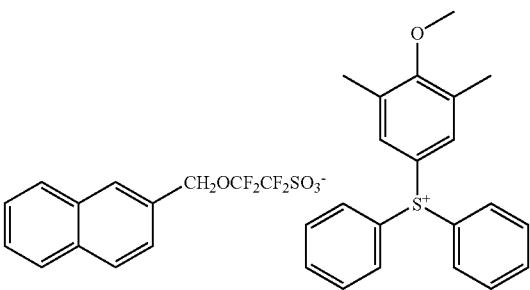
(b-12-20)
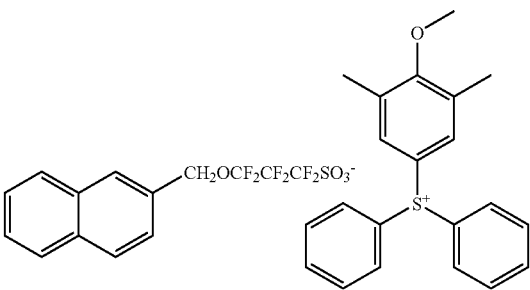
(b-12-21)
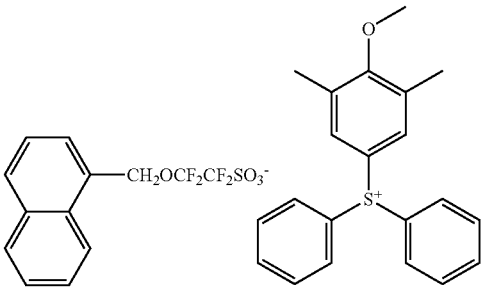

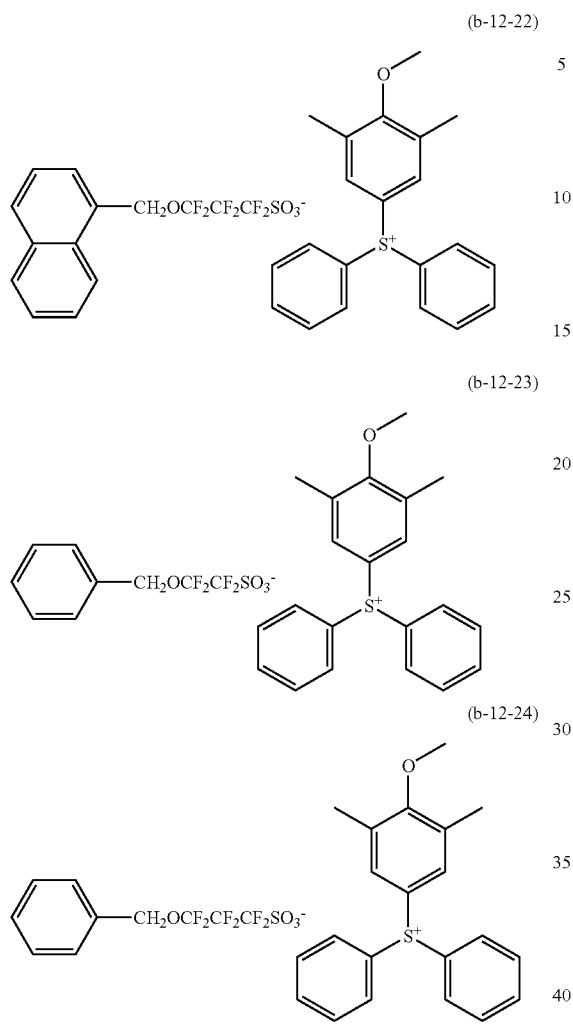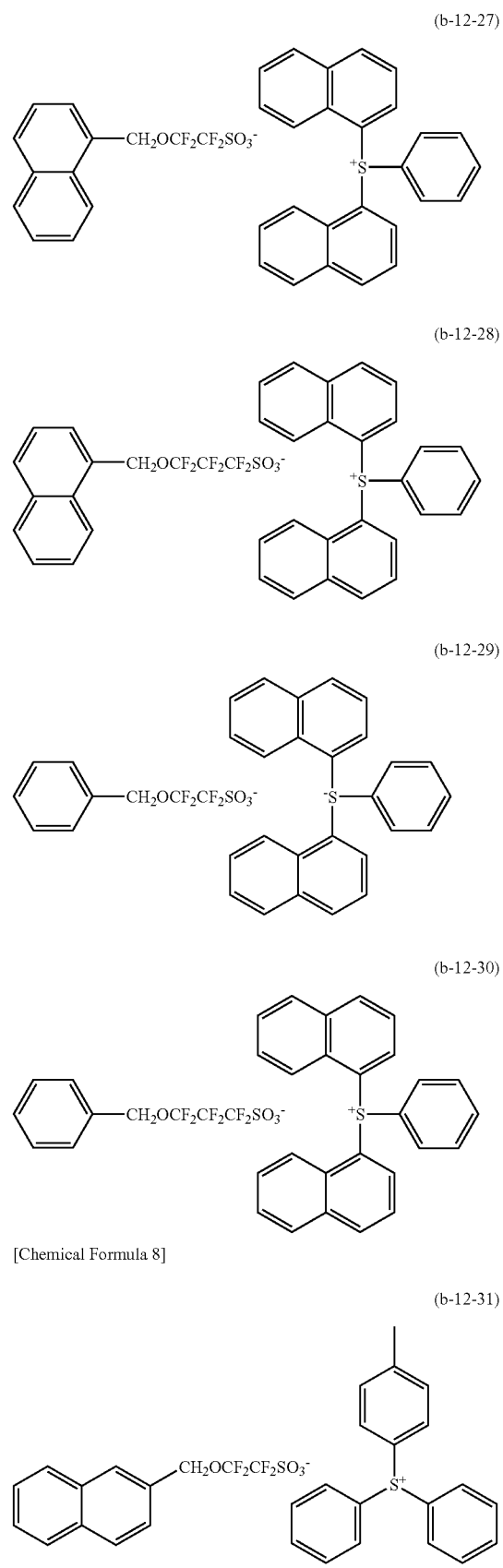
[Chemical Formula 7]
[Chemical Formula 8]

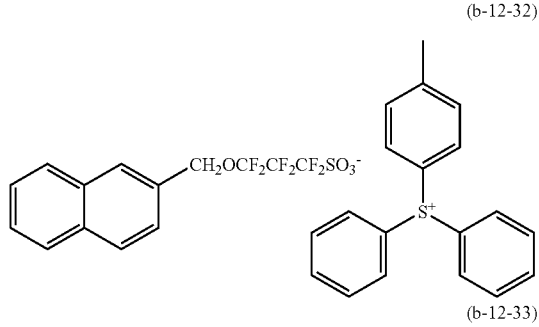

(b-12-32)

(b-12-33)

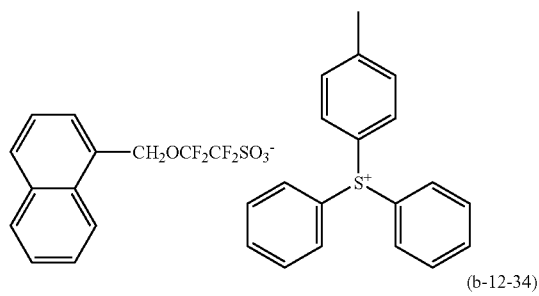

(b-12-34)

(b-12-35)

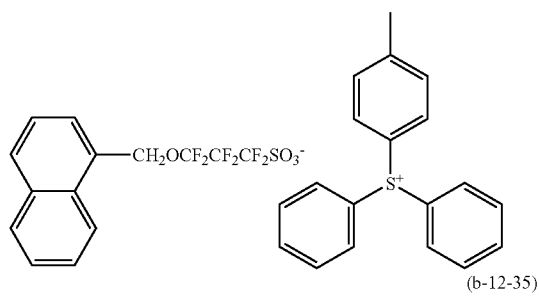

(b-12-36)

As a compound according to the first aspect of the present invention, compounds represented by formulas (b-12-1), (b-12-3), (b-12-5), (b-12-9), (b-12-13), (b-12-15), (b-12-17), (b-12-19), (b-12-21), (b-12-23), (b-12-25), (b-12-27), (b-12-29), (b-12-31), (b-12-33) and (b-12-35) are more preferable, and compounds represented by formulas (b-12-1), (b-12-3), (b-12-13), (b-12-19), (b-12-25) and (b-12-31) are particularly desirable.

<Synthesis Method of Compounds>

The compound (b1-12) according to the first aspect of the present invention can be produced, for example, as follows. A compound represented by general formula (b1-12-103) shown below is reacted with lithium hydroxide in an organic solvent such as tetrahydrofuran, acetone or methyl ethyl ketone, to obtain a compound represented by general formula (b1-12-104) shown below. Then, the obtained compound is reacted with a halogenide of a desired cation $A^+$ (e.g., $A^+Br^-$) in an aqueous solution, thereby obtaining the compound (b1-12).

[Chemical Formula 9]

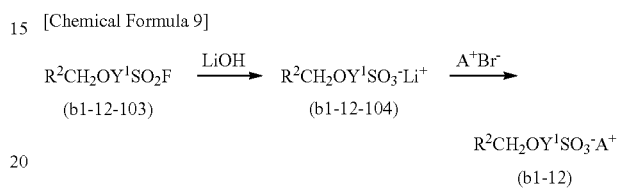

wherein $R^2$, $Y^1$ and $A^+$ are as defined for $R^2$, $Y^1$ and $A^+$ in general formula (b1-12) above.

The compound represented by the above general formula (b1-12-103) can be produced, for example, by referring to the method described in Example 1 of Published Japanese Translation No. Hei 11-502543 of the PCT International Publication. Specifically, for example, silver fluoride (AgF), a compound represented by general formula (b1-12-101) shown below and a compound represented by general formula (b1-12-102) shown below can be reacted in an organic solvent such as diglyme anhydride, thereby obtaining the compound represented by general formula (b1-12-103).

[Chemical Formula 10]

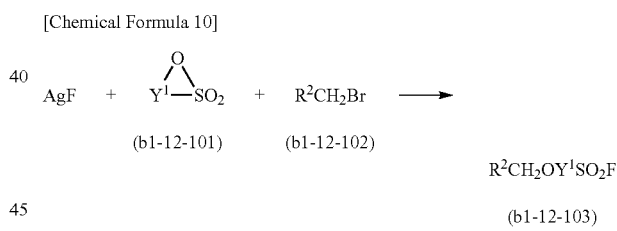

wherein $R^2$ and $Y^1$ are as defined for $R^2$ and $Y^1$ in general formula (b1-12) above.

The compound represented by the above general formula (b1-12-101) can be produced, for example, by a method described in Japanese Unexamined Patent Application, First Publication No. 2006-348382 or U.S. Pat. No. 6,624,328 B1. In consideration of the availability of the compound represented by general formula (b1-12-101), the alkylene group for $Y^1$ which may be fluorinated preferably has 2 to 4 carbon atoms, more preferably 2 or 3 carbon atoms, and most preferably 2 carbon atoms.

<<Acid Generator>>

The acid generator according to the second aspect of the present invention (hereafter, frequently referred to as "acid generator (B1)") includes a compound represented by general formula (b1-12) above. $R^2$, $Y^1$ and $A^+$ in the formula are defined as above for those described above in connection with the compound according to the first aspect of the present invention.

<<Resist Composition>>

The resist composition according to the third aspect of the present invention includes a base component (A) (hereafter, referred to as "component (A)") which exhibits changed solubility in an alkali developing solution under the action of acid and an acid-generator component (B) (hereafter, referred to as "component (B)") which generates acid upon exposure, and the component (B) includes an acid generator (B1) consisting of a compound represented by general formula (b1-12) above.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, frequently referred to as "low molecular weight compounds") and high molecular weight resins (polymeric materials) having a molecular weight of 2,000 or more. Generally, as the aforementioned low molecular weight compound, a non-polymer is used. With respect to the aforementioned resin (polymer), the "molecular weight" refers to the polystyrene equivalent weight average molecular weight determined by gel permeation chromatography (GPC). Hereafter, the simplified term "resin" refers to a resin having a molecular weight of 2,000 or more.

The component (A) may be either a resin that exhibits changed alkali solubility under the action of acid, or a low molecular weight material that exhibits changed alkali solubility under the action of acid.

When the resist composition of the present invention is a negative resist composition, as the component (A), a base component that is soluble in an alkali developing solution is used, and a cross-linking agent (C) is blended in the negative resist composition.

In the negative resist composition, during resist pattern formation, when acid is generated from the component (B) upon exposure, the action of this acid causes cross-linking between the base component and the cross-linking agent, and the cross-linked portion becomes alkali-insoluble.

Generally, as the component (A) for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base component which exhibits increased solubility in an alkali developing solution under the action of acid is used. The component (A) is insoluble in an alkali developing solution prior to exposure, and during formation of a resist pattern, when the acid generated from the component (B) by exposure acts upon the component (A), these acid dissociable, dissolution inhibiting groups dissociate, and the solubility of the entire component (A) in an alkali developing solution increases, so that the component (A) changes from an alkali-insoluble state to an alkali-soluble state. As a result, in the formation of a resist pattern, by conducting selective exposure of a resist film formed by applying the positive resist composition onto a substrate, the exposed portions become alkali-soluble, whereas the unexposed portions remain alkali-insoluble, and hence, a resist pattern can be formed by alkali developing.

In the resist composition of the present invention, the component (A) is preferably a base component which exhibits increased solubility in an alkali developing solution under action of acid. That is, the resist composition of the present invention is preferably a positive resist composition. Further, the component (A) is preferably a resin component (A1) (a polymeric material component) which exhibits increased solubility in an alkali developing solution under action of acid.

<Component (A1)>

The component (A) suitably used for such a positive resist composition is preferably a resin component (A1) (hereafter referred to as "component (A1)") and includes a structural unit (a1) derived from an acrylate ester containing an acid dissociable, dissolution inhibiting group.

Further, it is preferable that the component (A1) also have a structural unit (a2) derived from an acrylate ester having a lactone-containing cyclic group.

Moreover, it is preferable that the component (A1) also have a structural unit (a3) derived from an acrylate ester having a polar group-containing aliphatic hydrocarbon group.

Furthermore, it is preferable that the component (A1) also have a structural unit (a4) described below.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned.

With respect to the "structural unit derived from an acrylate ester", the "α-position (the carbon atom on the α-position)" refers to the carbon atom having the carbonyl group bonded thereto, unless specified otherwise.

The term "alkyl group" includes a linear, branched or cyclic, monovalent saturated hydrocarbon, unless otherwise specified.

A "lower alkyl group" is an alkyl group of 1 to 5 carbon atoms.

With respect to the acrylate ester, specific examples of the lower alkyl group for the substituent at the α-position include linear or branched lower alkyl groups such as a methyl group, ethyl group, propyl group, isopropyl group, n-butyl group, isobutyl group, tert-butyl group, pentyl group, isopentyl group, and neopentyl group.

Further, specific examples of the halogenated lower alkyl group include groups in which some or all of the hydrogen atoms of the aforementioned "lower alkyl group for the substituent at the α-position" are substituted with halogen atoms. Examples of the halogen atom include a fluorine atom, a chlorine atom, a bromine atom and an iodine atom, and a fluorine atom is particularly desirable.

In the present invention, it is preferable that a hydrogen atom, a lower alkyl group or a halogenated lower alkyl group, and more preferably a hydrogen atom, a lower alkyl group or a fluorinated lower alkyl group, be bonded to the α-position of the acrylate ester. In terms of industrial availability, a hydrogen atom or a methyl group is the most desirable.

Structural Unit (a1)

The structural unit (a1) is a structural unit derived from an acrylate ester containing an acid dissociable, dissolution inhibiting group.

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid or the like, and acetal-type acid dissociable, dissolution inhibiting groups such as alkoxyalkyl groups are widely known. Here, the term "(meth)acrylate ester" is a generic term that includes either or both of the acrylate ester having a hydrogen atom bonded to the α-position and the methacrylate ester having a methyl group bonded to the α-position.

Here, a "tertiary alkyl ester" describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic" is a relative concept used in relation to the term "aromatic", and defines a group or compound or the like that has no aromaticity.

The term "aliphatic branched" refers to a branched structure having no aromaticity. The "aliphatic branched, acid dissociable, dissolution inhibiting group" is not limited to be constituted from only carbon atoms and hydrogen atoms (not limited to hydrocarbon groups), but is preferably a hydrocarbon group. Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, a fluorine atom, fluorinated lower alkyl groups of 1 to 5 carbon atoms, and an oxygen atom (=O).

The basic ring of the "aliphatic cyclic group" exclusive of substituents is not limited to structures constituted from only carbon and hydrogen (not limited to hydrocarbon groups), but is preferably a hydrocarbon group. Further, the "hydrocarbon group" may be either saturated or unsaturated, but is preferably saturated.

Furthermore, the "aliphatic cyclic group" may be either a polycyclic group or a monocyclic group. Examples of the aliphatic cyclic group include groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cyclic alkyl group can be mentioned. Specific examples thereof include a 2-methyl-2-adamantyl group and a 2-ethyl-2-adamantyl group. Alternatively, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyloxy group (—C(O)—O—) in the structural units represented by general formulas (a1''-1) to (a1''-6) shown below, may also be exemplified.

[Chemical Formula 11]

(a1''-1)

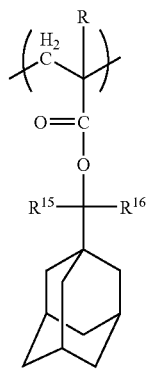

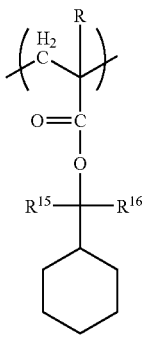

(a1″-2)

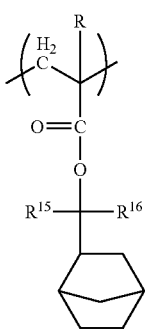

(a1″-3)

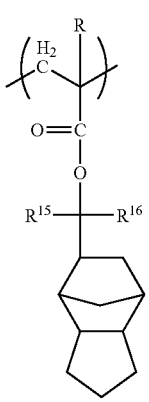

(a1″-4)

(a1″-5)

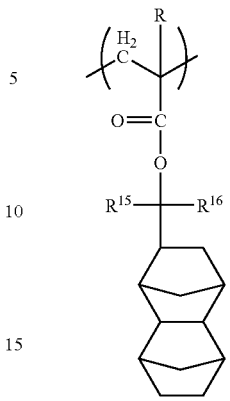

(a1″-6)

wherein R represents a hydrogen atom, a lower alkyl group or a halogenated lower alkyl group; and $R^{15}$ and $R^{16}$ each independently represents an alkyl group (which may be linear or branched, and preferably has 1 to 5 carbon atoms).

In general formulas (a1″-1) to (a1″-6) above, the lower alkyl group or halogenated lower alkyl group for R are defined as above for the lower alkyl group or halogenated lower alkyl group which may be bonded to the α-position of the aforementioned acrylate ester, and specific examples of the lower alkyl group or halogenated lower alkyl group for R are also the same as those exemplified above.

An "acetal-type acid dissociable, dissolution inhibiting group" generally substitutes a hydrogen atom at the terminal of an alkali-soluble group such as a carboxyl group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 12]

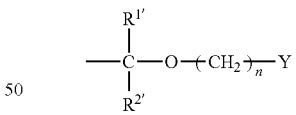

(p1)

wherein $R^{1'}$ and $R^{2'}$ each independently represents a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same as the lower alkyl groups for R above can be exemplified. As the lower alkyl group for $R^{1'}$ and $R^{2'}$, a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) be a group represented by general formula (p1-1) shown below.

[Chemical Formula 13]

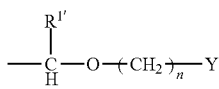

(p1-1)

wherein $R^{1'}$, n and Y are as defined above.

As the lower alkyl group for Y, the same as the lower alkyl groups for R above can be exemplified.

As the aliphatic cyclic group for Y, any of the aliphatic monocyclic or polycyclic groups which have been proposed for conventional ArF resists and the like can be appropriately selected for use. For example, the same groups as those described above in connection with the "aliphatic cyclic group" can be exemplified.

Further, as the acetal-type, acid dissociable, dissolution inhibiting group, groups represented by general formula (p2) shown below can also be exemplified.

[Chemical Formula 14]

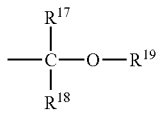

(p2)

wherein $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, wherein the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups (preferably having 1 to 5 carbon atoms). Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include a tetrahydropyranyl group and tetrahydrofuranyl group.

As the structural unit (a1), it is preferable to use at least one member selected from the group consisting of structural units represented by general formula (a1-0-1) shown below and structural units represented by general formula (a1-0-2) shown below.

[Chemical Formula 15]

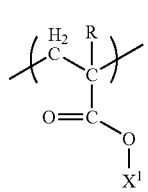

(a1-0-1)

wherein R represents a hydrogen atom, a lower alkyl group or a halogenated lower alkyl group; and $X^1$ represents an acid dissociable, dissolution inhibiting group.

[Chemical Formula 16]

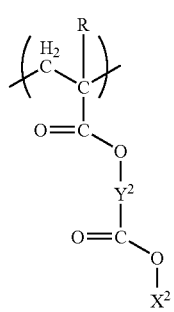

(a1-0-2)

wherein R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.

In general formula (a1-0-1) shown above, the lower alkyl group and halogenated lower alkyl group for R are defined as above for the lower alkyl group and halogenated lower alkyl group which may be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined above.

$X^2$ is the same as $X^1$ in general formula (a1-0-1), and examples thereof are also the same as those described above for $X^1$ in general formula (a1-0-1).

$Y^2$ is preferably an alkylene group of 1 to 4 carbon atoms or a divalent aliphatic cyclic group. As the aliphatic cyclic group, the same as those exemplified above in connection with the explanation of "aliphatic cyclic group" can be used, except that two hydrogen atoms have been removed therefrom.

Specific examples of the structural unit (a1) include structural units represented by general formulas (a1-1) to (a1-4) shown below.

[Chemical Formula 17]

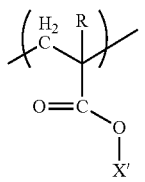
(a1-1)

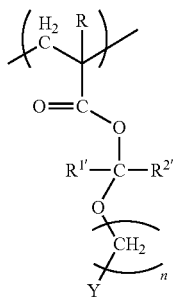
(a1-2)

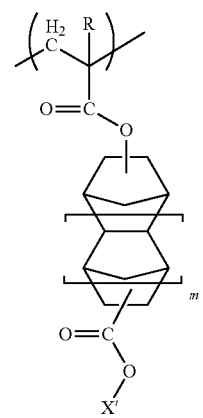
(a1-3)

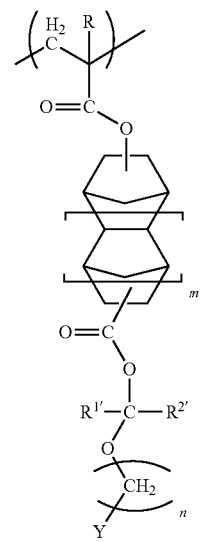
(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; m represents 0 or 1; R is as defined above; and $R^{1'}$ and $R^{2'}$ each independently represents a hydrogen atom or a lower alkyl group of 1 to 5 carbon atoms.

It is preferable that at least one of $R^{1'}$ and $R^{2'}$ represent a hydrogen atom, and it is more preferable that both of $R^{1'}$ and $R^{2'}$ represent a hydrogen atom. n is preferably 0 or 1.

Examples of the tertiary alkyl ester-type acid dissociable, dissolution inhibiting group for X' are the same as the above-exemplified tertiary alkyl ester-type acid dissociable, dissolution inhibiting groups for $X^1$.

Examples of the aliphatic cyclic group for Y are the same as those exemplified above in connection with the explanation of "aliphatic cyclic group".

Specific examples of structural units represented by general formula (a1-1) to (a1-4) above are shown below.

[Chemical Formula 18]

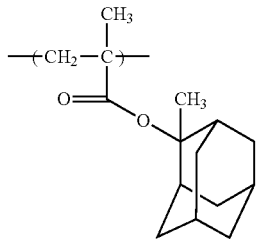
(a1-1-1)

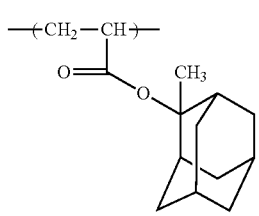
(a1-1-2)

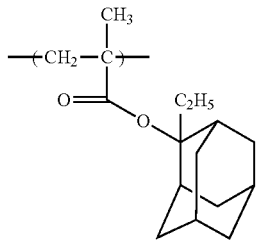
(a1-1-3)

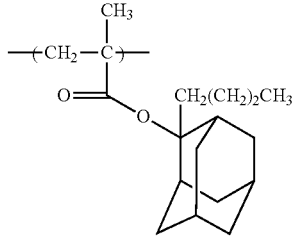
(a1-1-4)

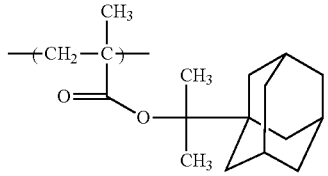
(a1-1-5)

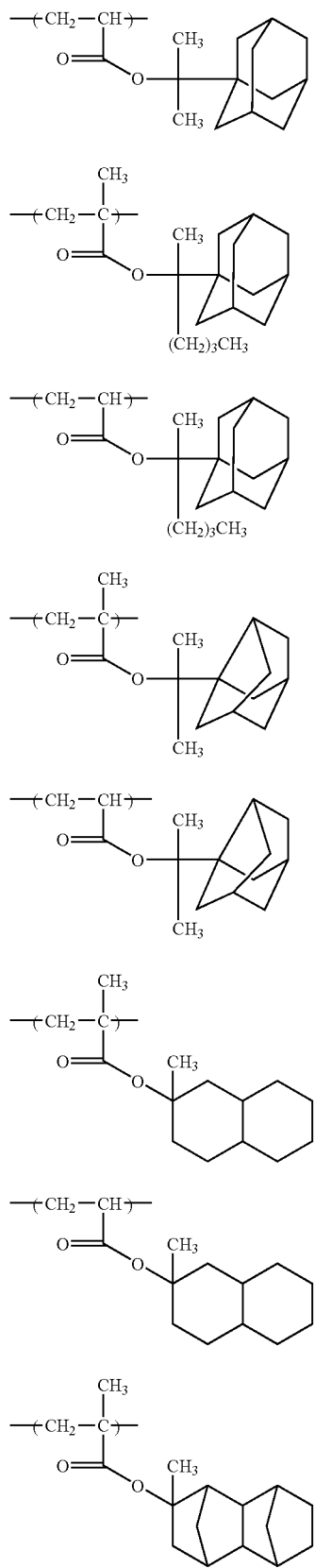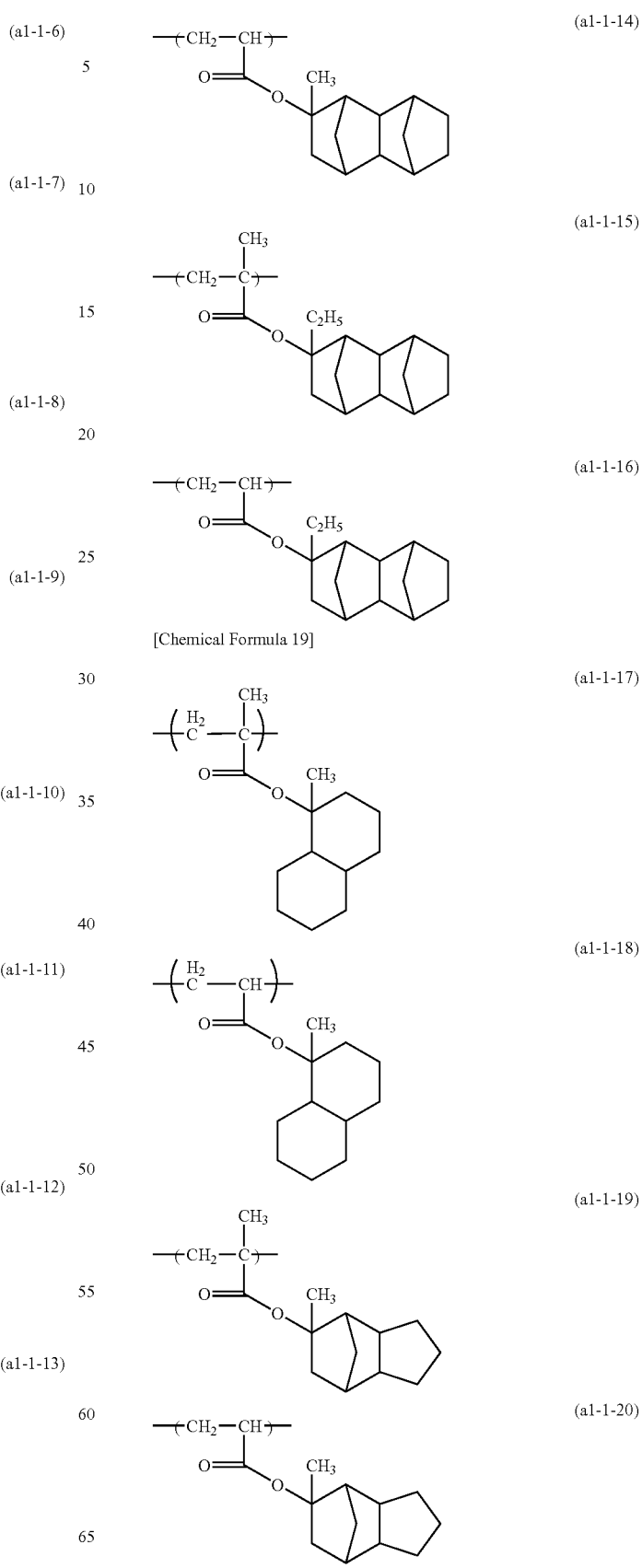

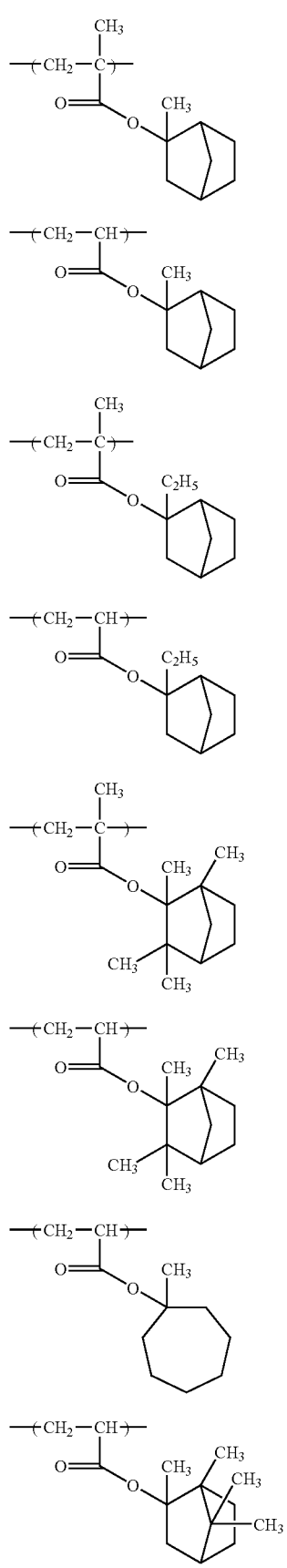
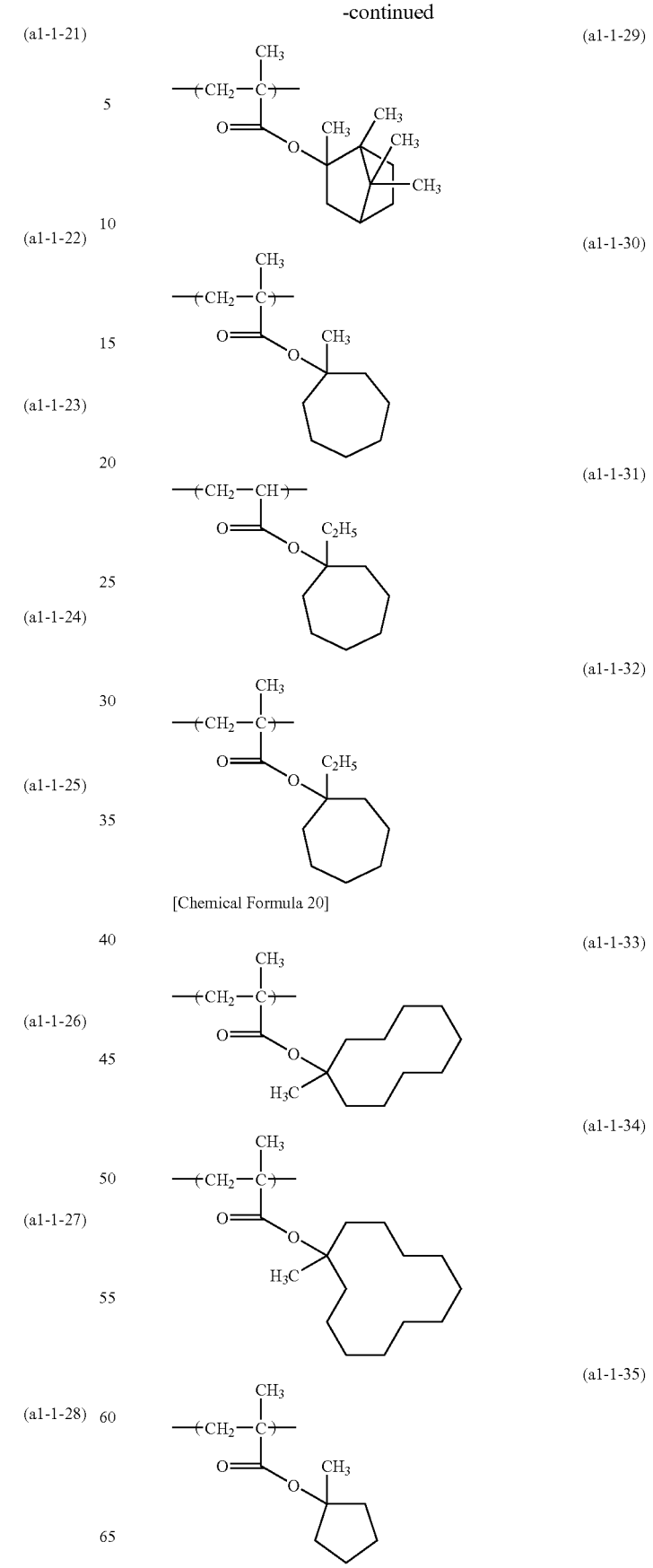
[Chemical Formula 20]

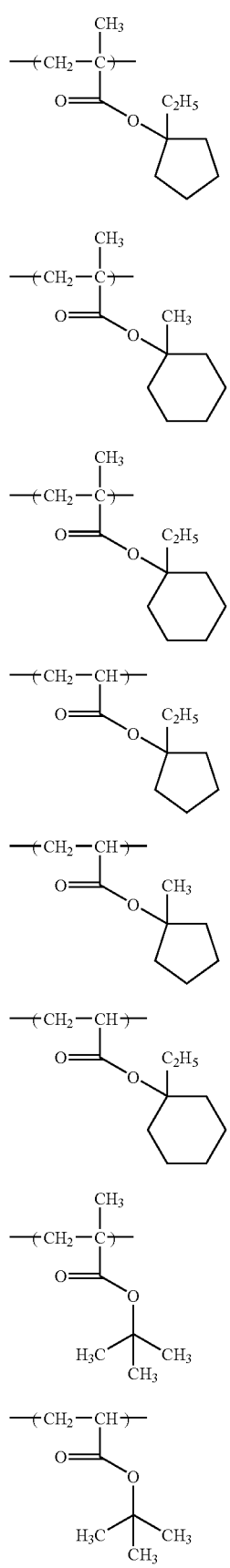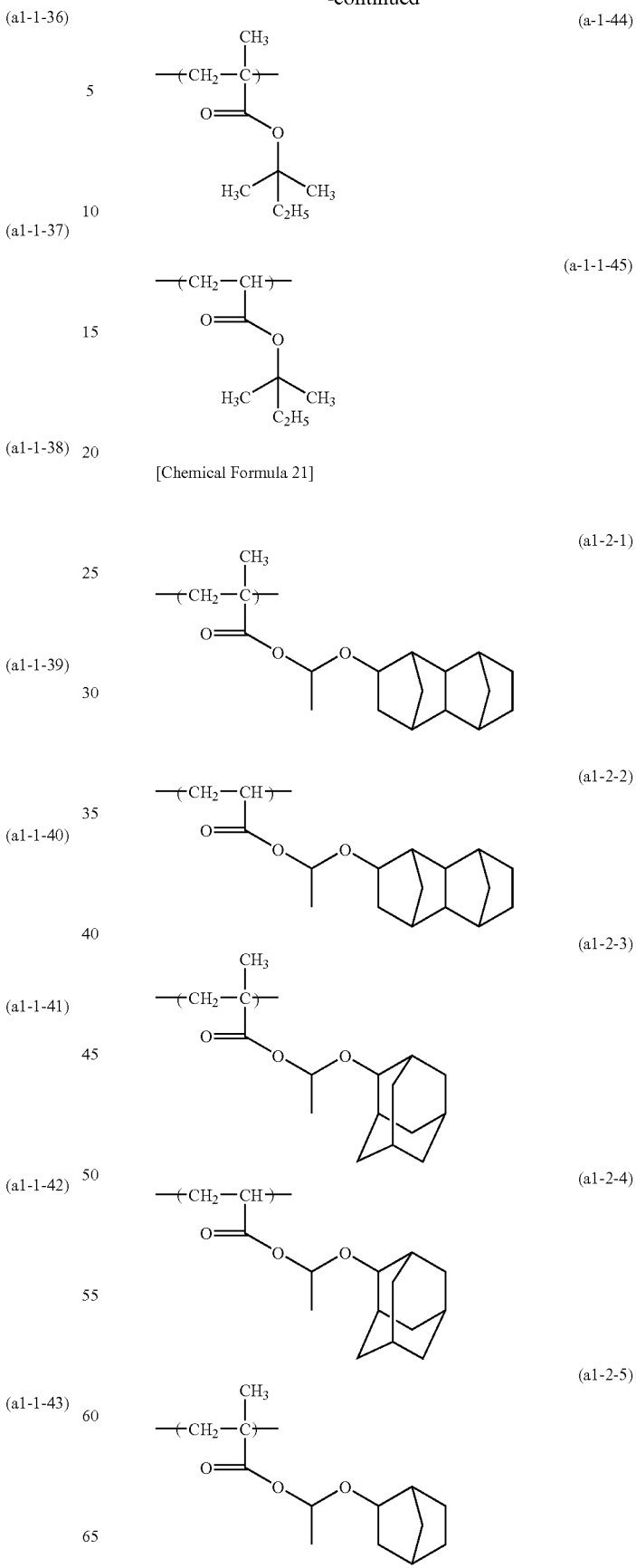

(a1-2-6)
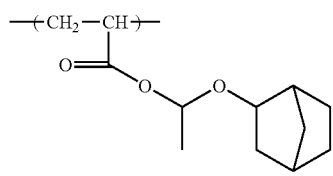
[Chemical Formula 22]
(a1-2-7)
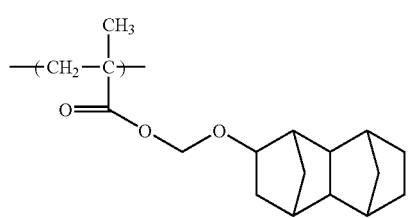
(a1-2-8)
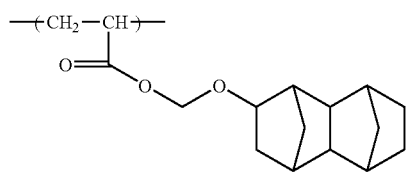
(a1-2-9)
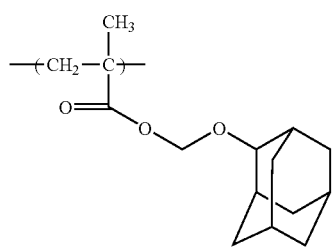
(a1-2-10)
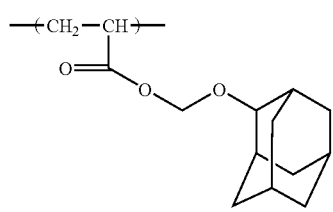
(a1-2-11)
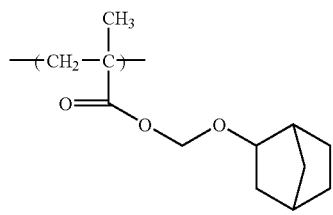
(a1-2-12)
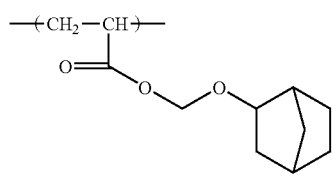
(a1-2-13)
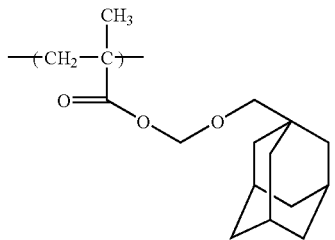
(a1-2-14)
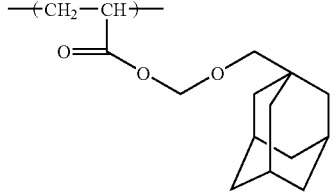
(a1-2-15)
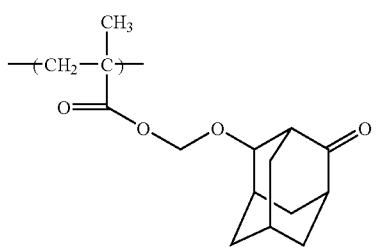
(a1-2-16)
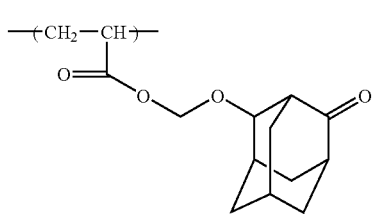
(a1-2-17)
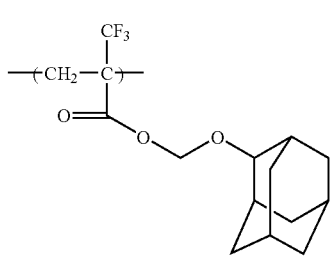
(a1-2-18)
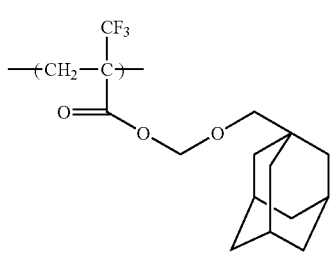
(a1-2-19)
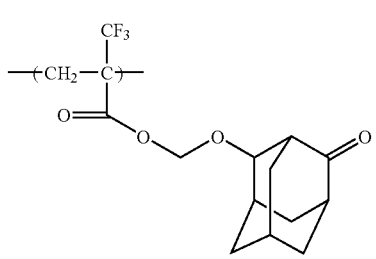

(a1-2-20)
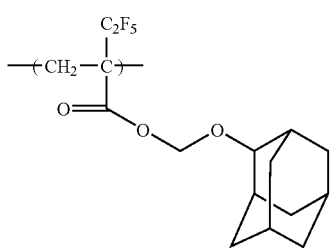
[Chemical Formula 23]
(a1-2-21)
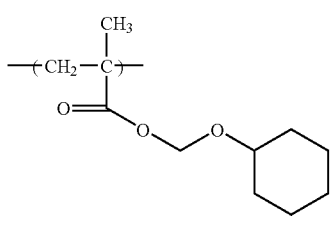
(a1-2-22)
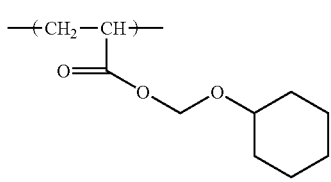
(a1-2-23)
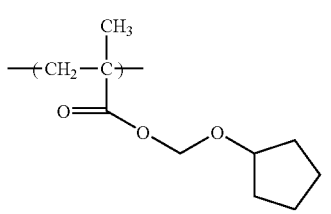
(a1-2-24)
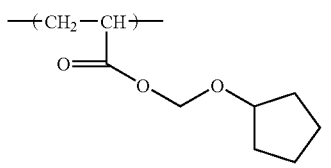
(a1-2-25)
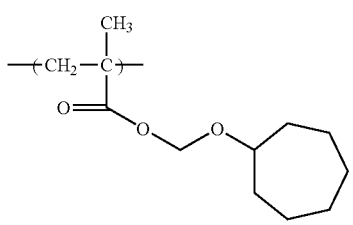
(a1-2-26)
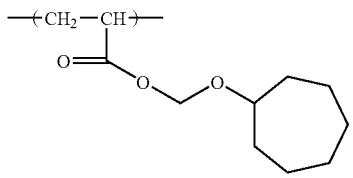
(a1-2-27)
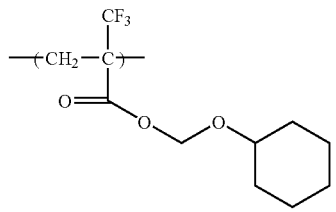
(a1-2-28)
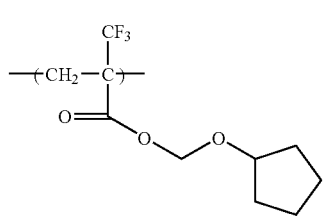
(a1-2-29)
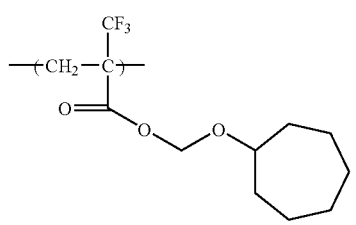
(a1-2-30)
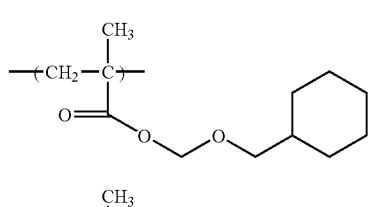
(a1-2-31)
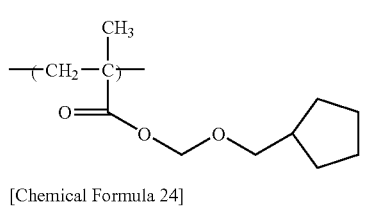
[Chemical Formula 24]
(a1-2-32)
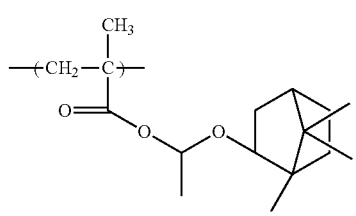
(a1-2-33)
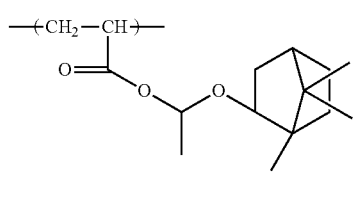
(a1-2-34)
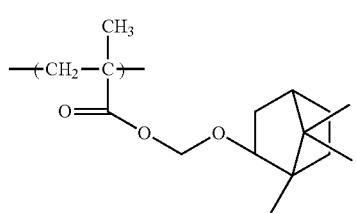

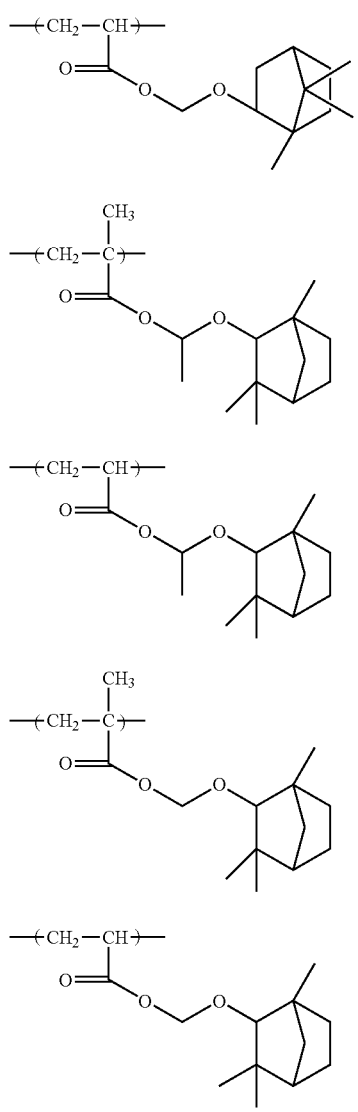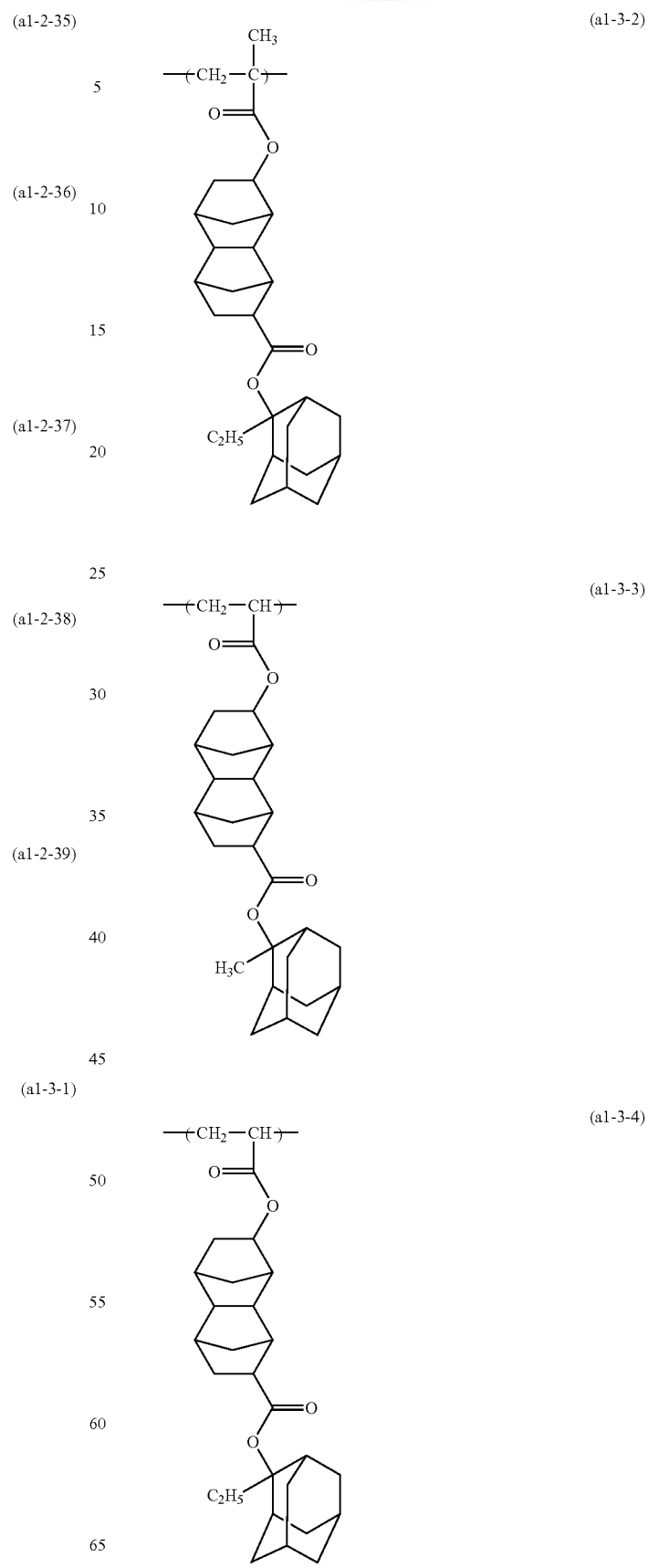

(a1-3-5)
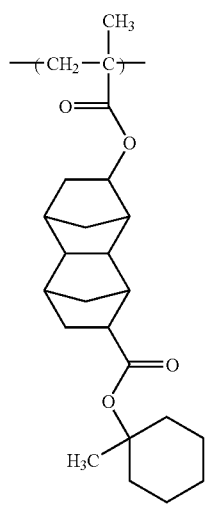
(a1-3-8)
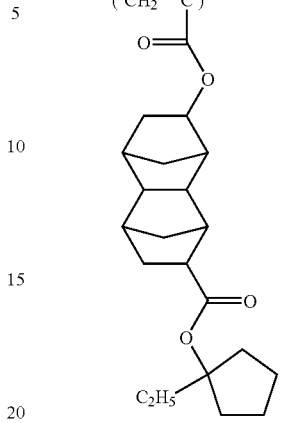
(a1-3-6)
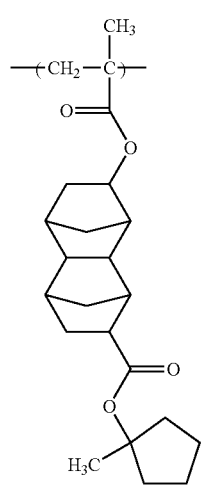
(a1-3-9)
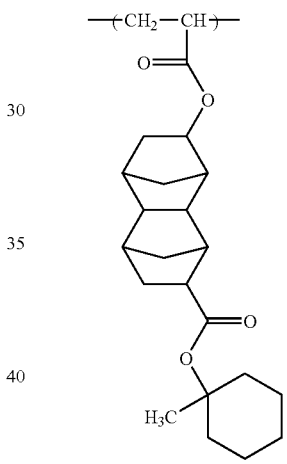
(a1-3-7)
(a1-3-10)
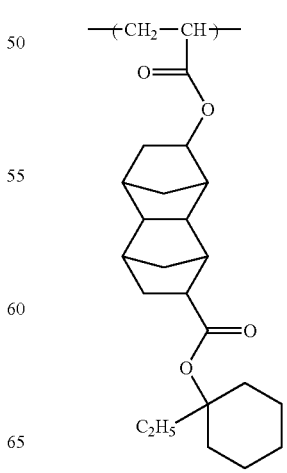

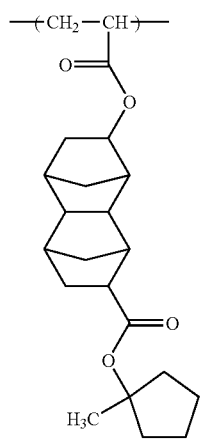 (a1-3-11)
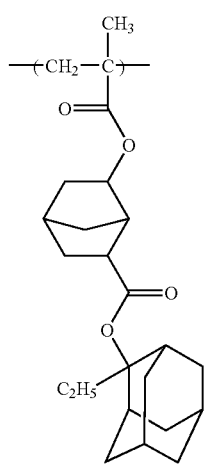 (a1-3-14)
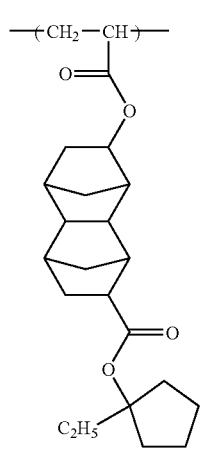 (a1-3-12)
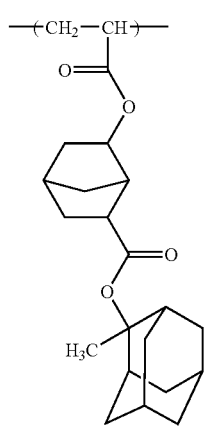 (a1-3-15)
[Chemical Formula 26]
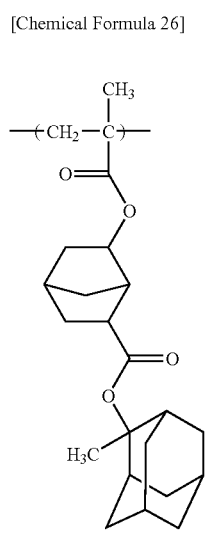 (a1-3-13)
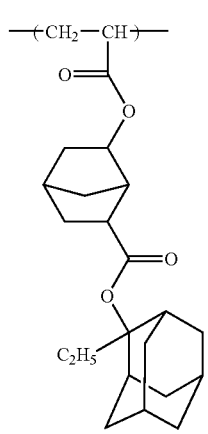 (a1-3-16)

-continued
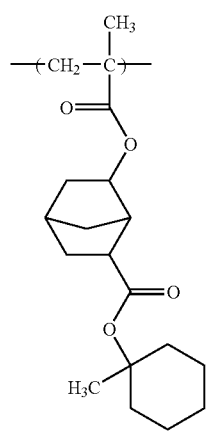
(a1-3-17)
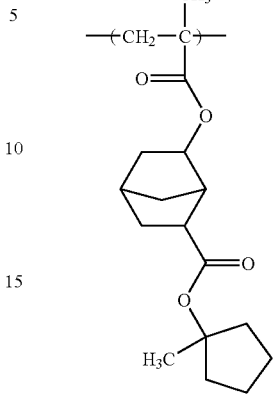
(a1-3-21)
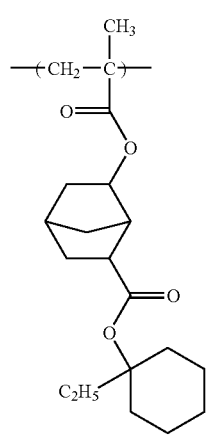
(a1-3-18)
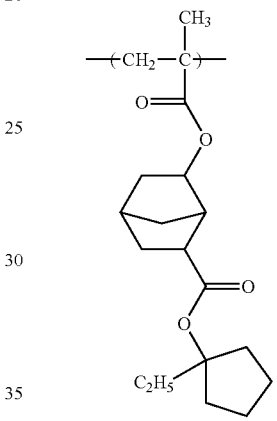
(a1-3-22)
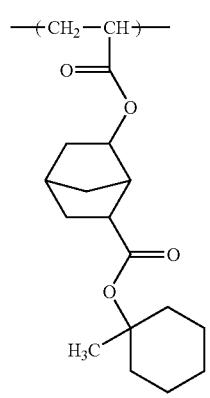
(a1-3-19)
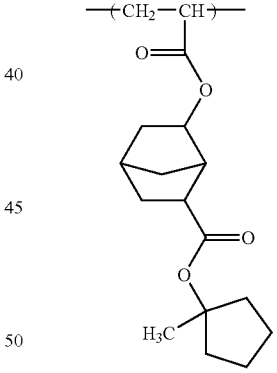
(a1-3-23)
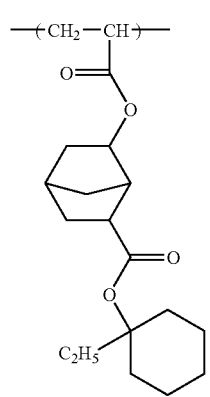
(a1-3-20)
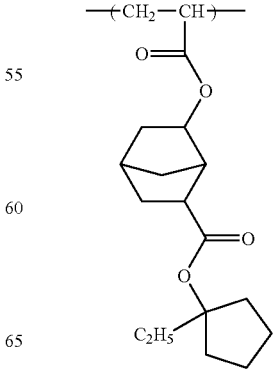
(a1-3-24)

[Chemical Formula 27]
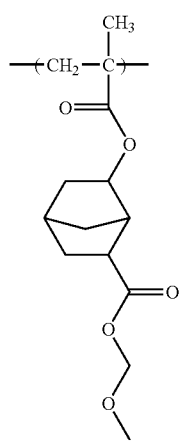
(a1-4-1)
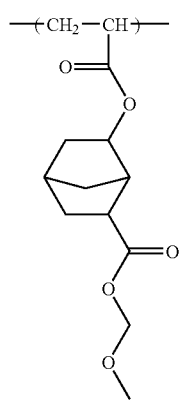
(a1-4-2)
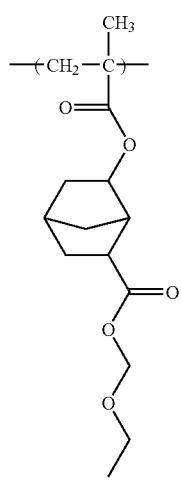
(a1-4-3)
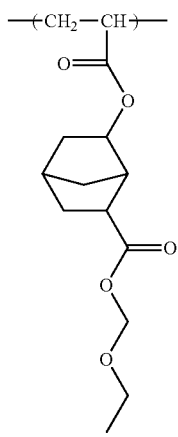
(a1-4-4)
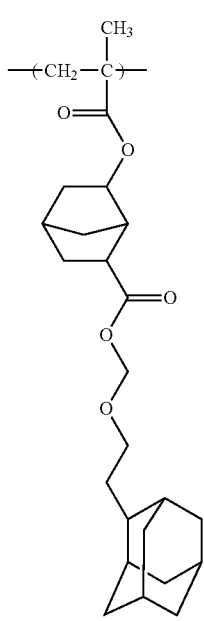
(a1-4-5)
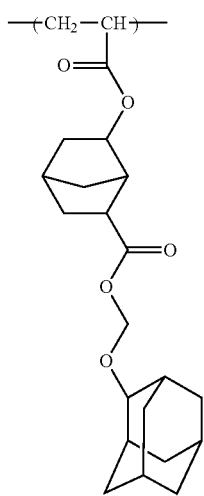
(a1-4-6)

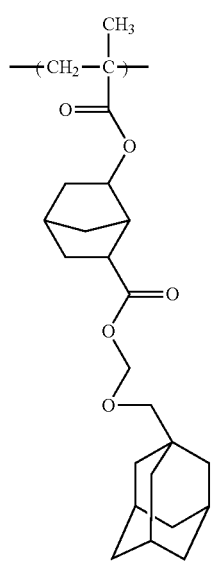
(a1-4-7)
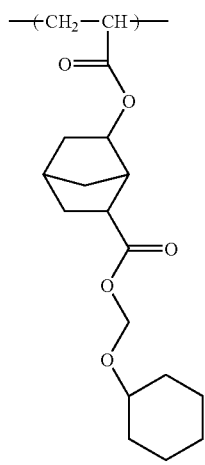
(a1-4-10)
(a1-4-8)
(a1-4-11)
(a1-4-9)
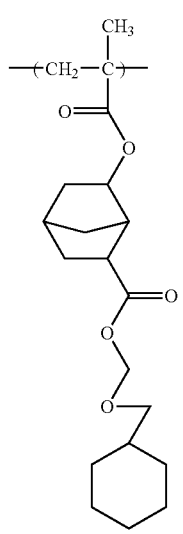
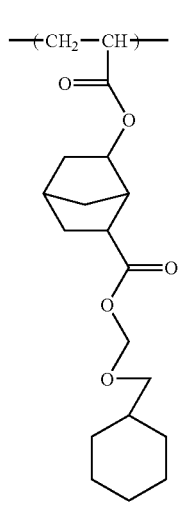
(a1-4-12)

(a1-4-13)
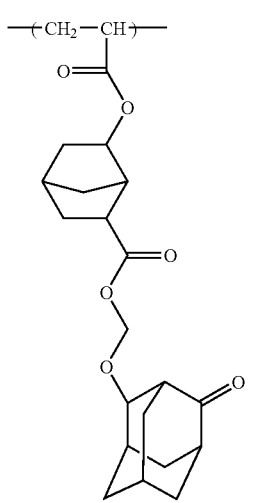
(a1-4-14)
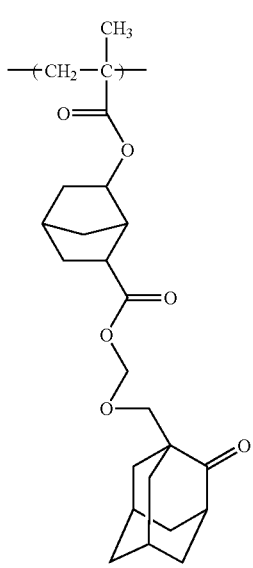
(a1-4-15)
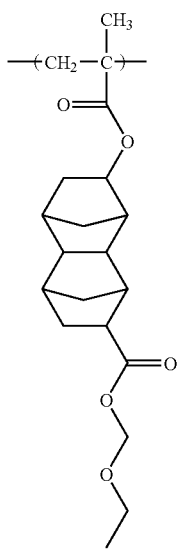
[Chemical Formula 28]
(a1-4-16)
(a1-4-17)

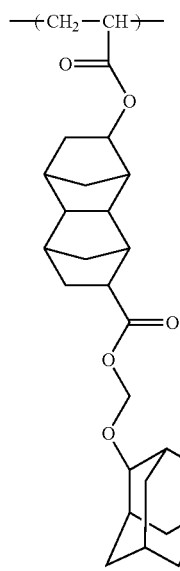
(a1-4-18)
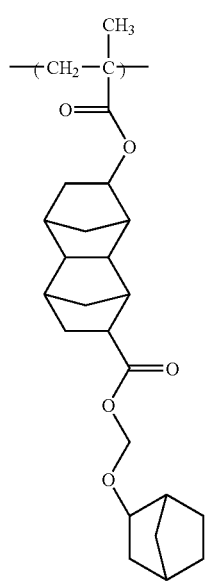
(a1-4-19)
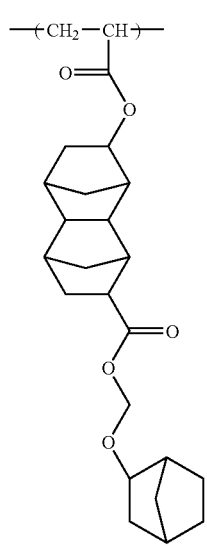
(a1-4-20)
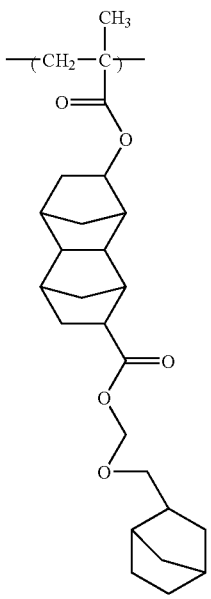
(a1-4-21)
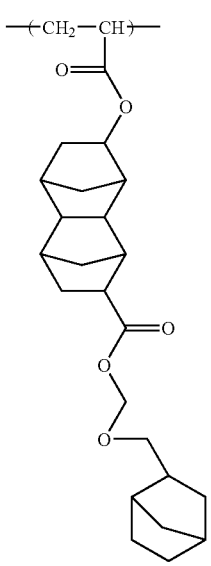
(a1-4-22)

(a1-4-23)
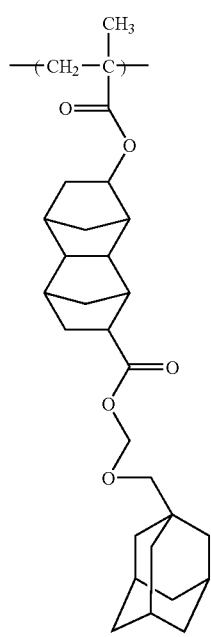
(a1-4-25)
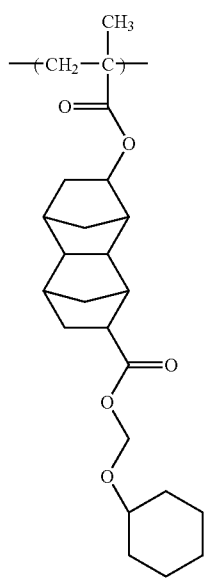
(a1-4-24)
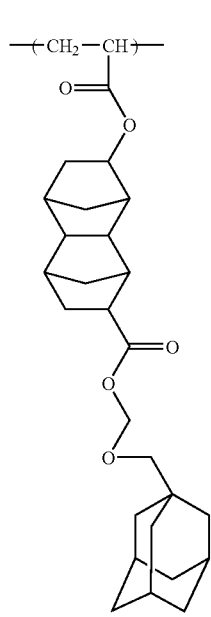
(a1-4-26)
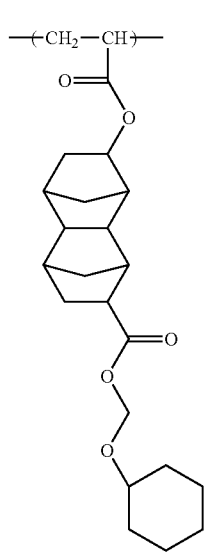

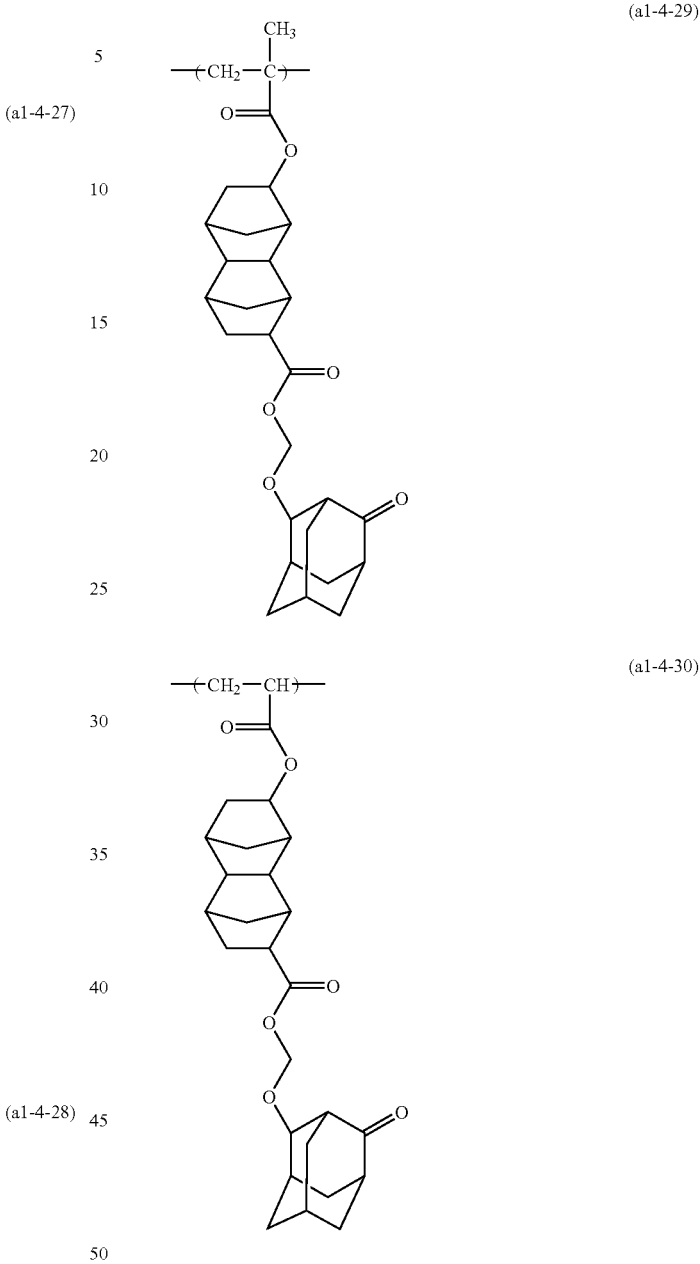

As the structural unit (a1), one type of structural unit may be used alone, or two or more types may be used in combination.

Among these, structural units represented by general formula (a1-1) are preferable. More specifically, at least one structural unit selected from the group consisting of structural units represented by formulas (a1-1-1) to (a-1-1-6) and (a1-1-35) to (a1-1-41) is more preferable.

Further, as the structural unit (a1), structural units represented by general formula (a1-1-01) shown below, which include the structural units represented by formulas (a1-1-1) to (a1-1-4), and structural units represented by general formula (a1-1-02) shown below, which include the structural units represented by formulas (a1-1-35) to (a1-1-41), are also preferable.

[Chemical Formula 29]

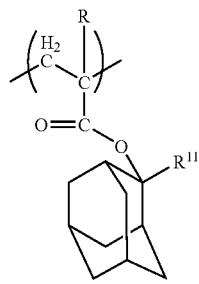

(a1-1-01)

wherein R represents a hydrogen atom, a lower alkyl group or a halogenated lower alkyl group; and $R^{11}$ represents a lower alkyl group.

[Chemical Formula 30]

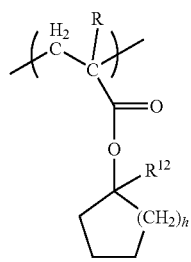

(a1-1-02)

wherein R represents a hydrogen atom, a lower alkyl group or a halogenated lower alkyl group; $R^{12}$ represents a lower alkyl group; and h represents an integer of 1 to 3.

In general formula (a1-1-01), R is as defined above. The lower alkyl group for $R^{11}$ is the same as the lower alkyl group for R above, and is preferably a methyl group or an ethyl group.

In general formula (a1-1-02), R is as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as the lower limit of the above-mentioned range, a pattern can be easily formed using a resist composition prepared from the component (A1). On the other hand, by making the amount of the structural unit (a1) no more than the upper limit of the above-mentioned range, a good balance can be achieved with the other structural units.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 31]

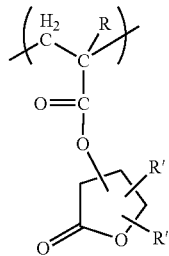

(a2-1)

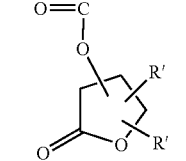

(a2-2)

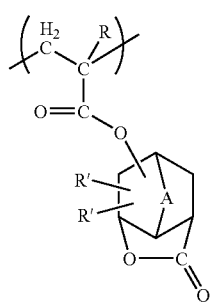

(a2-3)

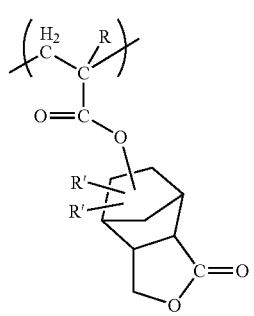

(a2-4)

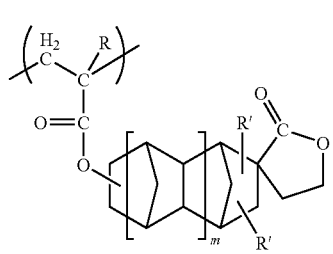

-continued (a2-5)

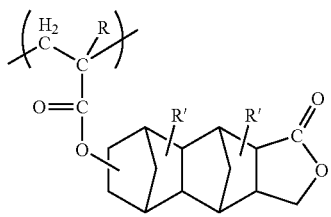

wherein R represents a hydrogen atom, a lower alkyl group or a halogenated lower alkyl group; R' represents a hydrogen atom, a lower alkyl group or an alkoxy group of 1 to 5 carbon atoms; m represents an integer of 0 or 1; and A represents an alkylene group of 1 to 5 carbon atoms or an oxygen atom.

In general formulas (a2-1) to (a2-5), R is defined as above for R in the structural unit (a1).

As the lower alkyl group for R', the same as the lower alkyl groups for R above in the structural unit (a1) can be exemplified.

Specific examples of alkylene groups of 1 to 5 carbon atoms for A include a methylene group, ethylene group, n-propylene group and isopropylene group.

In the structural units represented by general formulas (a2-1) to (a2-5), in consideration of industrial availability, R' is preferably a hydrogen atom.

Specific examples of structural units represented by general formulas (a2-1) to (a2-5) above are shown below.

[Chemical Formula 32]

(a2-1-1)

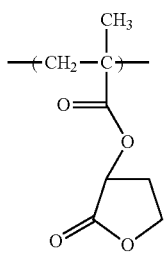

(a2-1-2)

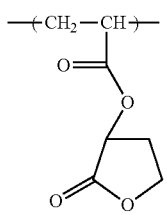

(a2-1-3)

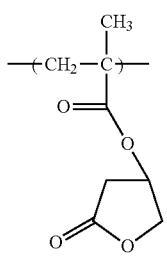

(a2-1-4)

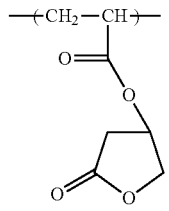

(a2-1-5)

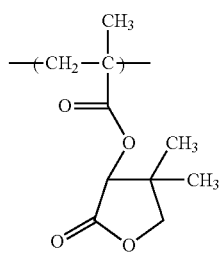

(a2-1-6)

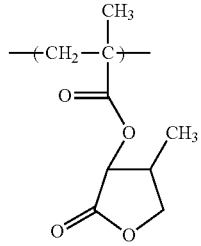

[Chemical Formula 33]

(a2-2-1)

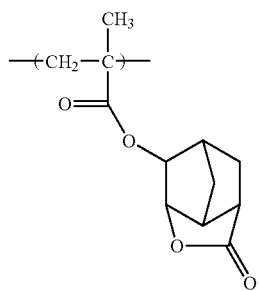

(a2-2-2)

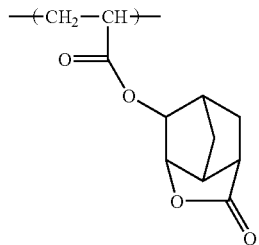

(a2-2-3)

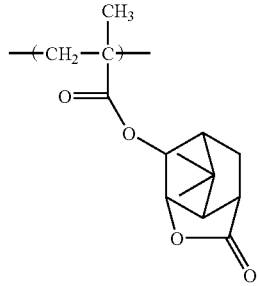

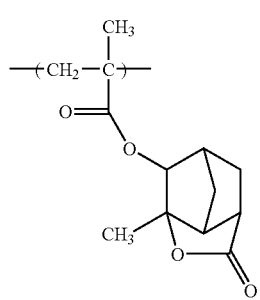 (a2-2-4)
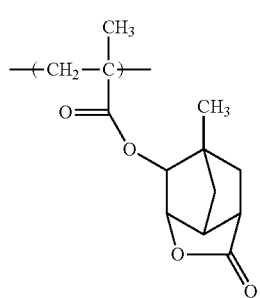 (a2-2-5)
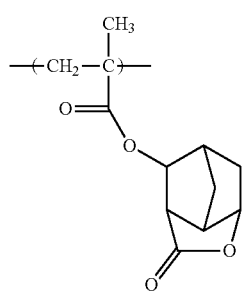 (a2-2-6)
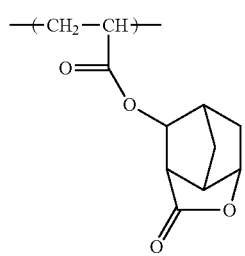 (a2-2-7)
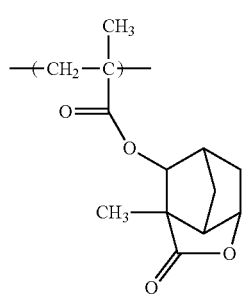 (a2-2-8)
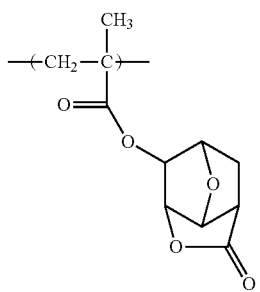 (a2-2-9)
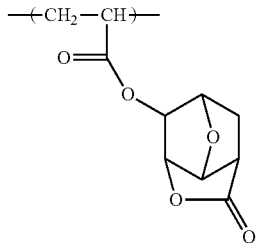 (a2-2-10)
[Chemical Formula 34]
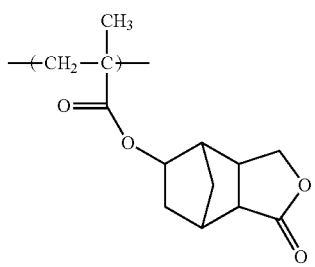 (a2-3-1)
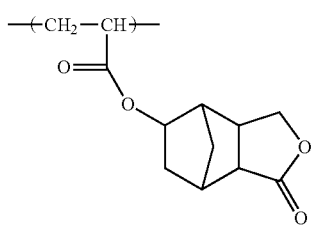 (a2-3-2)
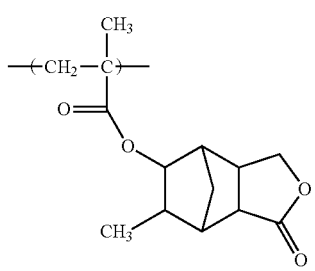 (a2-3-3)
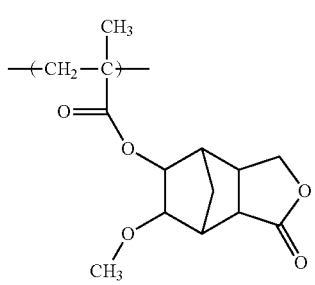 (a2-3-4)

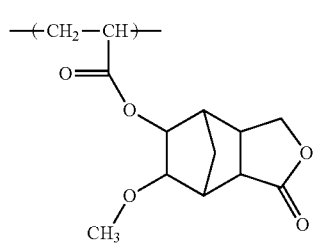 (a2-3-5)
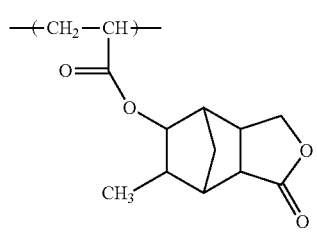 (a2-3-6)
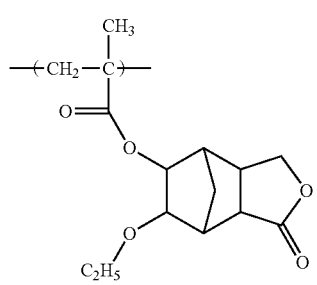 (a2-3-7)
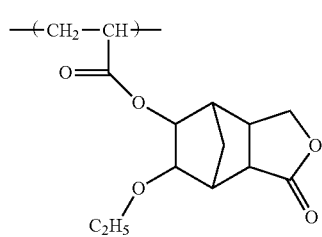 (a2-3-8)
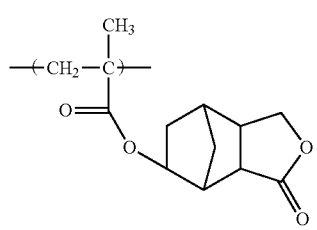 (a2-3-9)
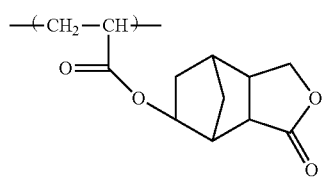 (a2-3-10)
[Chemical Formula 35]
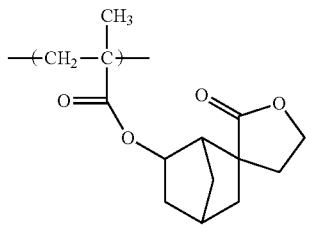 (a2-4-1)
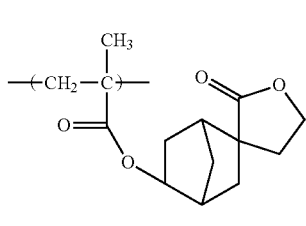 (a2-4-2)
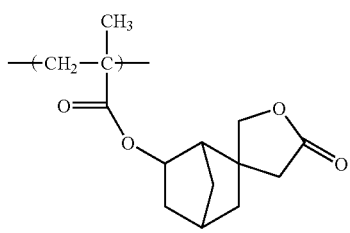 (a2-4-3)
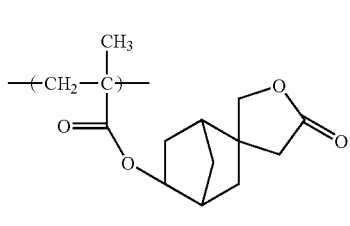 (a2-4-4)
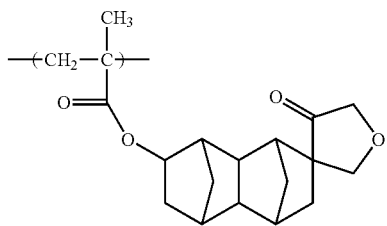 (a2-4-5)
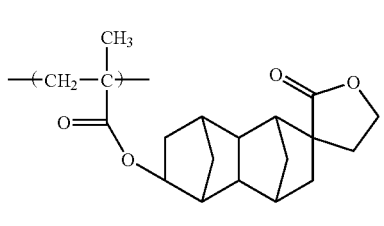 (a2-4-6)
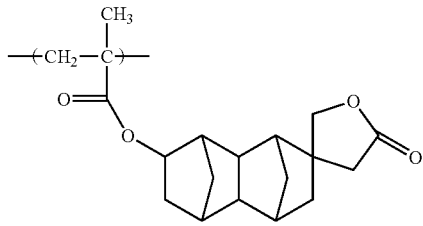 (a2-4-7)

(a2-4-8) 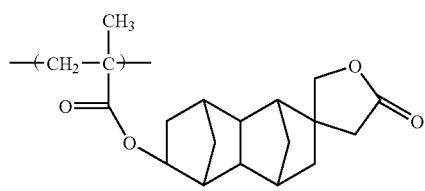

(a2-4-9) 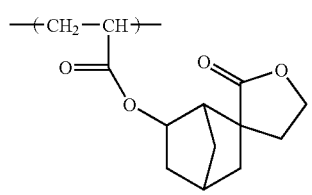

(a2-4-10) 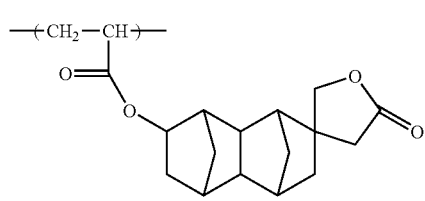

(a2-4-11) 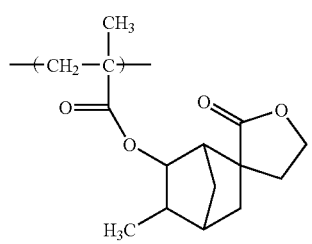

[Chemical Formula 36]

(a2-4-12) 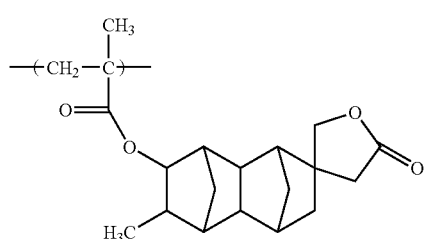

(a2-5-1) 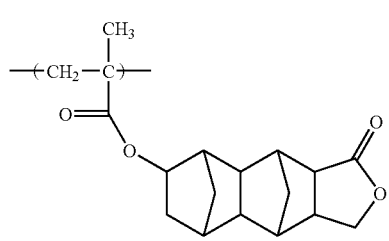

(a2-5-2) 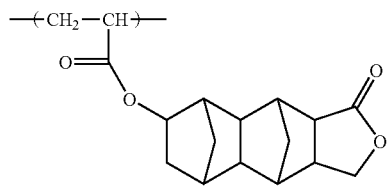

(a2-5-3) 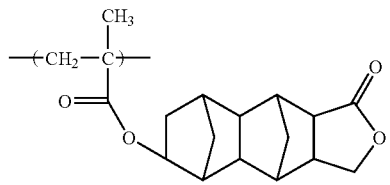

(a2-5-4) 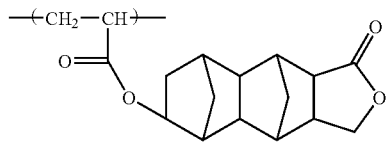

(a2-5-5) 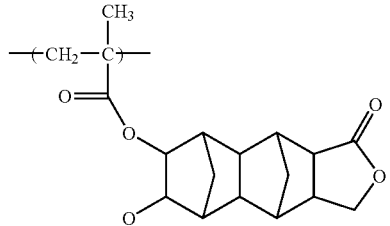

(a2-5-6) 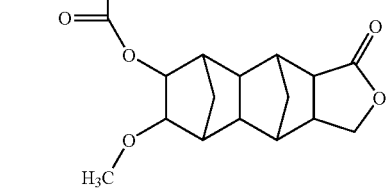

In the component (A1), as the structural unit (a2), one type of structural unit may be used alone, or two or more types may be used in combination.

As the structural unit (a2), it is preferable to use at least one structural unit selected from the group consisting of the aforementioned general formulas (a2-1) to (a2-5), and it is more preferable to use at least one structural unit selected from the group consisting of general formulas (a2-1) to (a2-3). Of these, it is particularly desirable to use at least one structural unit selected from the group consisting of chemical formulas (a2-1-1), (a2-1-2), (a2-2-1), (a2-2-2), (a2-3-1), (a2-3-2), (a2-3-9) and (a2-3-10).

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as the lower limit of the above-mentioned range, the effect of using the structural unit (a2) can be satisfactorily achieved. On the other hand, by making the amount of the structural unit (a2) no more than the upper limit of the above-mentioned range, a good balance can be achieved with the other structural units.

Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane or tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. Here, the term "acrylic acid" is a generic term that includes acrylic acids having a hydrogen atom bonded to the carbon atom on the α-position, and acrylic acids having a substituent (an atom other than a hydrogen atom or a group) bonded to the carbon atom on the α-position. As the substituent, a lower alkyl group or a halogenated lower alkyl group can be mentioned.

When the hydrocarbon group is a polycyclic group, structural units represented by formulas (a3-1), (a3-2), and (a3-3) shown below are preferable.

[Chemical Formula 37]

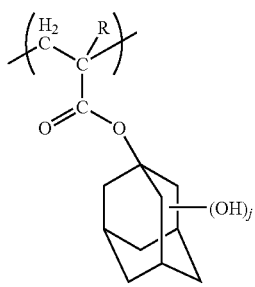

(a3-1)

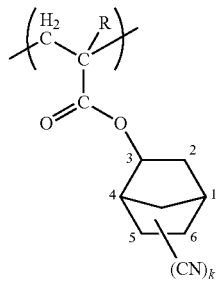

(a3-2)

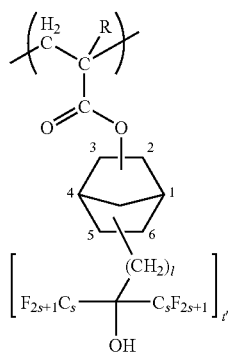

(a3-3)

wherein R is as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1, l is preferably 1 and s is preferably 1. Further, in formula (a3-3), it is preferable that a 2-norbornyl group or 3-norbornyl group be bonded to the terminal of the carboxy group of the acrylic acid. The fluorinated alkyl alcohol is preferably bonded to the 5th or 6th position of the norbonyl group.

In the component (A1), as the structural unit (a3), one type of structural unit may be used alone, or two or more types may be used in combination.

Structural Unit (a4)

The component (A1) may also have a structural unit (a4) which is different to the above-mentioned structural units (a1) to (a3), as long as the solubility in an alkali developing solution caused by the action of acid is not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 38]

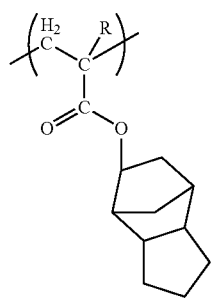
(a4-1)

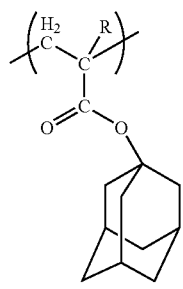
(a4-2)

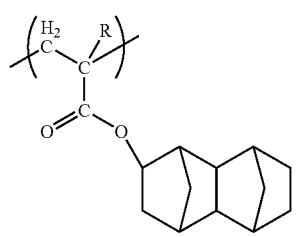
(a4-3)

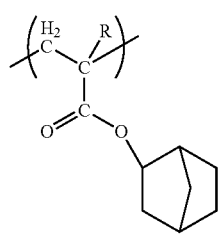
(a4-4)

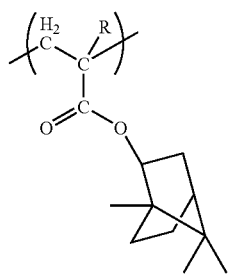
(a4-5)

wherein R is as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

In the present invention, the component (A1) preferably includes the structural units (a1), (a2) and (a3), and more preferably includes the structural units (a1), (a2), (a3) and (a4). The component (A1) preferably includes a copolymer composed of the structural units (a1), (a2) and (a3), and most preferably includes a copolymer composed of the structural units (a1), (a2), (a3) and (a4).

In the component (A), as the component (A1), one type of component may be used alone, or two or more types may be used in combination.

In the present invention, as the component (A1), it is particularly desirable to include a copolymer having 3 structural units represented by formula (A1-11) or (A1-21) shown below.

[Chemical Formula 39]

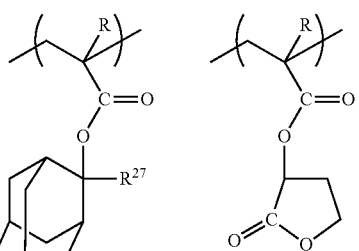
(A1-11)

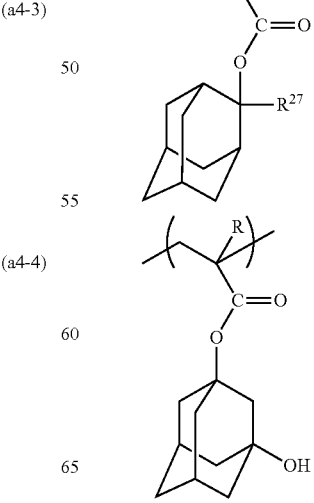

-continued

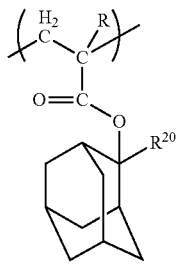

(A1-21)

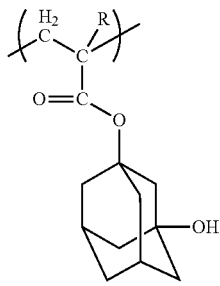

wherein R is as defined above, and the plurality of R may be either the same or different from each other; $R^{27}$ represents a lower alkyl group; and $R^{20}$ represents a lower alkyl group.

In formula (A-11), as the lower alkyl group for $R^{27}$, the same as the lower alkyl group for R can be exemplified. As $R^{27}$, a methyl group or an ethyl group is preferable, and a methyl group is particularly desirable.

In formula (A1-21), as the lower alkyl group for $R^{20}$, the same as the lower alkyl group for R can be exemplified. As $R^{20}$, a methyl group or an ethyl group is preferable, and an ethyl group is particularly desirable.

The component (A1) can be obtained, for example, by a conventional radical polymerization or the like of the monomers corresponding to each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH during the above polymerization, a —$C(CF_3)_2$—OH group can be introduced at the terminals of the component (A1). Such a copolymer having an introduced hydroxyalkyl group in which some of the hydrogen atoms of the alkyl group are substituted with fluorine atoms is effective in reducing the development of defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than the upper limit of the above-mentioned range, the component (A1) exhibits satisfactory solubility in a resist solvent when used as a resist. On the other hand, by making the weight average molecular weight at least as large as the lower limit of the above-mentioned range, dry etching resistance and cross-sectional shape of the resist pattern become satisfactory.

Further, the dispersity (Mw/Mn) is preferably 1.0 to 5.0, more preferably 1.0 to 3.0, and most preferably 1.2 to 2.5. Here, Mn is the number average molecular weight.

<Component (B)>

In the resist composition of the present invention, the component (B) contains an acid generator (B1) (hereafter, referred to as "component (B1)") including a compound represented by general formula (b1-12) shown above; $R^2$—$CH_2$—O—$Y^1$—$SO_3^-A^+$.

$R^2$, $Y^1$ and $A^+$ in the formula are defined as above for those described above with respect to the compound according to the first aspect of the present invention, and specific examples thereof are also the same as those described above.

By including the component (B1) within the component (B), a satisfactory resist pattern can be formed using the resist composition of the present invention.

As the component (B), one type of acid generator may be used alone, or two or more types may be used in combination.

In the resist composition of the present invention, the amount of the component (B1) based on the entire component (B) is preferably 40% by weight or more, more preferably 70% by weight or more, and may be even 100% by weight. It is particularly desirable that the amount of the component (B1) within the component (B) be 100% by weight. It is preferable to make the amount of the component (B1) at least as large as the lower limit of the above-mentioned range, because when a resist pattern is formed using the resist composition of the present invention, exposure margin (EL margin) described below can be increased, and excellent lithography properties can be achieved.

In the component (B), an acid generator (B2) other than the aforementioned component (B1) (hereafter, referred to as "component (B2)") may be used in combination with the component (B1).

As the component (B2), there is no particular limitation as long as it is an acid generator other than the component (B1), and any of the known acid generators used in conventional chemically amplified resist compositions can be used.

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As the onium salt-based acid generator, a compound represented by general formula (b-1) or (b-2) shown below can be used.

[Chemical Formula 40]

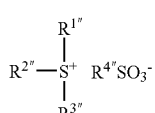

(b-1)

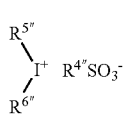

(b-2)

wherein $R^{1''}$ to $R^{3''}$, $R^{5''}$ and $R^{6''}$ each independently represents an aryl group or alkyl group, wherein two of $R^{1''}$ to $R^{3''}$ in formula (b-1) may be bonded to each other to form a ring with the sulfur atom in the formula; and $R^{4''}$ represents a linear, branched or cyclic alkyl group or fluorinated alkyl group, with the proviso that at least one of $R^{1''}$ to $R^{3''}$ represents an aryl group, and at least one of $R^{5''}$ and $R^{6''}$ represents an aryl group.

$R^{1''}$ to $R^{3''}$ in general formula (b-1) are defined as above for $R^{1'''}$ to $R^{3'''}$ in general formula (b'-1) described above with respect to the compound according to the first aspect of the present invention, and specific examples thereof are also the same as those described above.

$R^{5''}$ and $R^{6''}$ in general formula (b-2) are defined as above for $R^{5'''}$ and $R^{6'''}$ in general formula (b'-2) described above with respect to the compound according to the first aspect of the present invention, and specific examples thereof are also the same as those described above.

$R^{4''}$ represents a linear, branched or cyclic alkyl group or fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{1''}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms. Further, the fluorination ratio of the fluorinated alkyl group (the percentage of fluorine atoms within the alkyl group) is preferably from 10 to 100%, more preferably from 50 to 100%, and it is particularly desirable that all hydrogen atoms be substituted with fluorine atoms (namely, the fluorinated alkyl group be a perfluoroalkyl group) because the acid strength increases.

$R^{4''}$ is most preferably a linear or cyclic alkyl group or fluorinated alkyl group.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalen-1-yl)tetrahydrothiophenium trifluoromethanesulfonate, heptafluoropropanesulfonate or nonafluorobutanesulfonate; 1-(4-ethoxynaphthalen-1-yl)tetrahydrothiophenium trifluoromethanesulfonate, heptafluoropropanesulfonate or nonafluorobutanesulfonate; 1-(4-n-butoxynaphthalen-1-yl)tetrahydrothiophenium trifluoromethanesulfonate, heptafluoropropanesulfonate or nonafluorobutanesulfonate; 1-phenyhetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may also be used.

[Chemical Formula 41]

wherein X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group for X" or those of the alkyl group for Y" and Z" within the above-mentioned range of the number of carbon atoms, the better, because the solubility in a resist solvent is improved.

Further, in the alkylene group for X" or the alkyl group for Y" and Z", it is preferable that the number of hydrogen atoms substituted with fluorine atoms be as large as possible because the acid strength increases and the transparency to high energy radiation of 200 nm or less or electron beam is improved. The amount of fluorine atoms within the alkylene group or alkyl group, i.e., fluorination ratio, is preferably from 70 to 100%, more preferably from 90 to 100%, and it is particularly desirable that the alkylene group or alkyl group be a perfluoroalkylene or perfluoroalkyl group in which all hydrogen atoms are substituted with fluorine atoms.

Furthermore, as the onium salt-based acid generator, a sulfonium salt having a cation moiety represented by general formula (b-5) or (b-6) shown below may also be used.

[Chemical Formula 42]

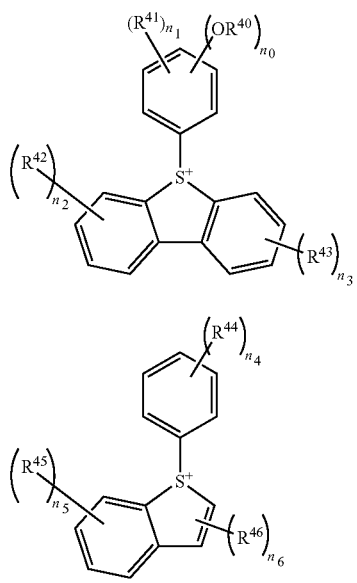

wherein $R^{40}$ represents a hydrogen atom, an alkyl group, an alkoxyalkyl group or an alkoxycarbonylalkyl group; $R^{41}$ represents an alkyl group, an acetyl group, a carboxyl group or a hydroxyalkyl group; each of $R^{42}$ to $R^{46}$ independently represents an alkyl group, an acetyl group, an alkoxy group, a carboxyl group or a hydroxyalkyl group; each of no to $n_5$ independently represents an integer of 0 to 3, with the proviso that $n_0+n_1$ is 5 or less; and $n_6$ represents an integer of 0 to 2.

$R^{40}$ to $R^{46}$ and $n_0$ to $n_6$ in general formulas (b-5) and (b-6) are defined as above for $R^{40}$ to $R^{46}$ and $n_0$ to $n_6$ described above with respect to the aforementioned compound, and specific examples thereof are also the same as those described above.

The anion moiety of the sulfonium salt having a cation moiety represented by general formula (b-5) or (b-6) is not particularly limited, and the same anion moieties as those used within previously proposed onium salt-based acid generators may be used. Examples of such anion moieties include fluorinated alkylsulfonic acid ions such as anion moieties ($R^{4''}SO_3^-$) for onium salt-based acid generators represented by general formula (b-1) or (b-2) shown above; and anion moieties represented by general formula (b-3) or (b-4) shown above. Among these, fluorinated alkylsulfonic acid ions are preferable, more preferably fluorinated alkylsulfonic acid ions of 1 to 4 carbon atoms, and linear perfluoroalkylsulfonic acid ions of 1 to 4 carbon atoms are particularly desirable. Specific examples include a trifluoromethylsulfonic acid ion, heptafluoro-n-propylsulfonic acid ion and nonafluoro-n-butylsulfonic acid ion.

In the present description, an oxime sulfonate-based acid generator is a compound having at least one group represented by general formula (B-1) shown below, and has a feature of generating acid by irradiation. Such oxime sulfonate-based acid generators are widely used for a chemically amplified resist composition, and can be appropriately selected.

[Chemical Formula 43]

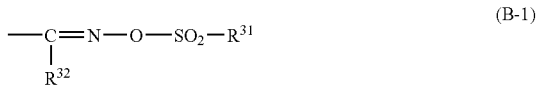

wherein $R^{31}$ and $R^{32}$ each independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "have a substituent" means that some or all of the hydrogen atoms of the alkyl group or the aryl group are substituted with substituents.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 44]

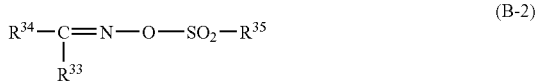
(B-2)

wherein $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 45]

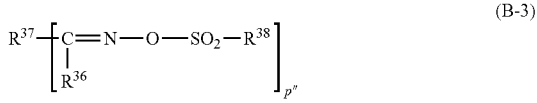
(B-3)

wherein $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group and a phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group or halogenated alkyl group as the substituent preferably has 1 to 8 carbon atoms, and more preferably 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, and still more preferably 90% or more. A completely fluorinated alkyl group in which 100% of the hydrogen atoms are substituted with fluorine atoms is particularly desirable.

In general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be exemplified.

[Chemical Formula 46]

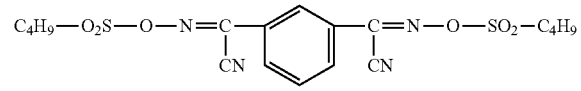

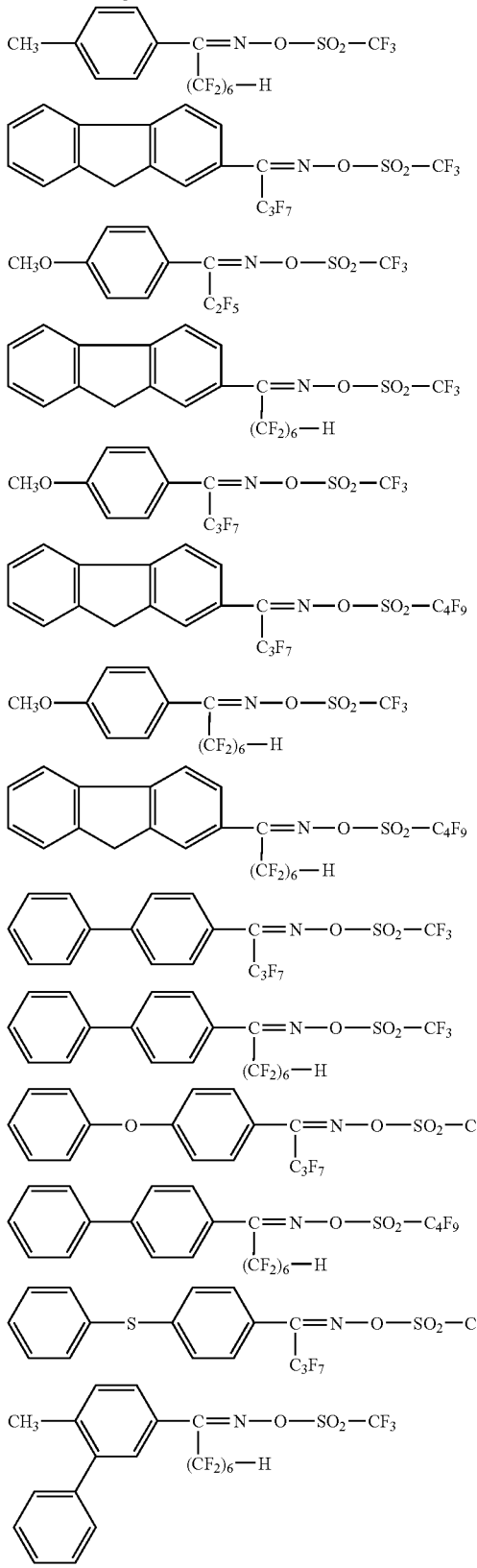

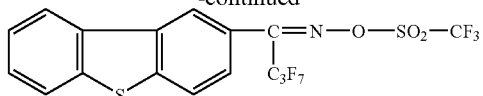
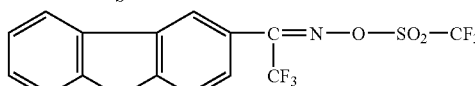
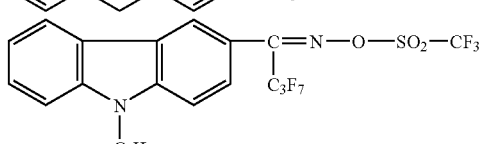
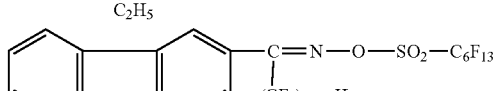
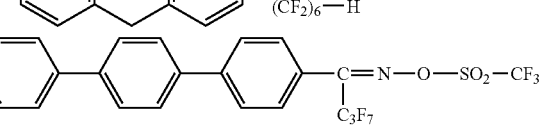

Among the above-exemplified compounds, the following 4 compounds are preferable.

[Chemical Formula 48]

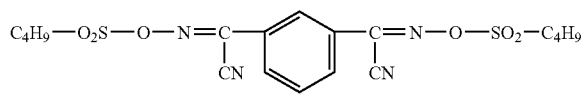
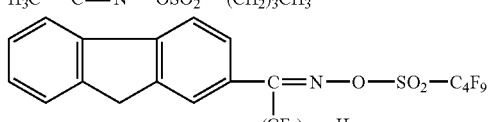
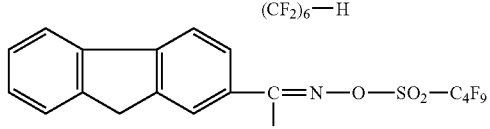

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be exemplified.

As the component (B2), one type of acid generator may be used alone, or two or more types may be used in combination.

The total amount of the component (B) within the resist composition of the present invention is typically 0.5 to 30 parts by weight, and preferably 1 to 20 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Component (C)>

In the resist composition of the present invention, for suppressing footing of the resist pattern and obtaining satisfactory resist patterns, it is preferable to add a compound (C) (hereafter referred to as the component (C)) represented by general formula (c-1) shown below.

[Chemical Formula 49]

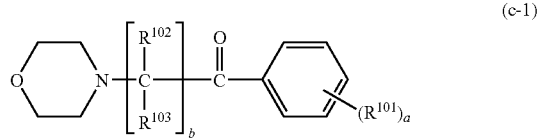

(c-1)

In general formula (c-1), $R^{101}$ is a group represented by general formula (I) shown below (hereafter, this group is referred to as "group (I)").

[Chemical Formula 50]

(I)

In general formula (I), $R^{104}$ represents a hydrogen atom or an alkyl group of 1 to 5 carbon atoms, and examples of the alkyl group include linear or branched lower alkyl groups such as a methyl group, ethyl group, propyl group, isopropyl group, n-butyl group, isobutyl group, tert-butyl group, pentyl group, isopentyl group or neopentyl group. The alkyl group for $R^{104}$ is preferably an alkyl group of 1 to 5 carbon atoms, and most preferably a methyl group.

$R^{105}$ is an alkylene group of 1 to 5 carbon atoms, and the alkylene group is preferably a linear or branched alkylene group of 1 to 5 carbon atoms, and a methylene group is particularly desirable.

c is 0 or 1. If c is 0, $R^{104}$ is preferably an alkyl group of 1 to 5 carbon atoms, more preferably an alkyl group of 1 to 3 carbon atoms, and most preferably a methyl group. If c is 1, $R^{104}$ is preferably a hydrogen atom.

In general formula (c-1), a is an integer of 1 to 3, preferably 1 or 2, and most preferably 1.

The bonding positions of the group (I) with respect to the benzene ring shown in general formula (c-1) are not particularly limited. If a is 1, in other words, when one group (I) is bonded to the benzene ring, the bonding position of the group (I) is preferably the para position or meta position, more preferably para position relative to the bonding position of a carbonyl group positioned next to the benzene ring.

If a is 2 or 3, in other words, when the plurality of groups (I) are present, the plurality of groups (I) may be the same or different from each other.

b is an integer of 1 to 3, preferably 1 or 2, and most preferably 1.

$R^{102}$ and $R^{103}$ each independently represents a hydrogen atom, or a linear alkyl group of 1 to 5 carbon atoms, and the alkyl group is defined as above for the alkyl group for $R^{104}$ described above, and specific examples thereof are also the same as those described above.

In the present invention, in terms of achieving superior effects in suppressing footing of the resist pattern, it is preferable that both of $R^{102}$ and $R^{103}$ represent an alkyl group. It is presumed that because the carbon atom to which $R^{102}$ and $R^{103}$ are bonded is a tertiary carbon atom, the structure thereof is changed by light upon exposure, thereby considerably increasing the pKa value, as compared to the pKa value prior to exposure.

The alkyl group for $R^{102}$ and $R^{103}$ may be the same or different.

As the component (C), a compound in which $R^{102}$ and $R^{103}$ represent an alkyl group of 1 to 5 carbon atoms and b represents 1 is particularly desirable.

The component (C) may further have a substituent on the benzene ring shown in the aforementioned general formula (c-1). The expression "have a substituent" means that at least one hydrogen atom bonded to a carbon atom that constitutes the benzene ring has been substituted with the substituent. As the substituent, an alkyl group is preferable, and an alkyl group of 1 to 5 carbon atoms is more preferable.

Specific examples of the component (C) include compounds represented by chemical formulas (c-1-1) to (c-1-5) shown below. Among these, compounds represented by formulas (c-1-1), (c-1-2) and (c-1-3) are preferable.

[Chemical Formula 51]

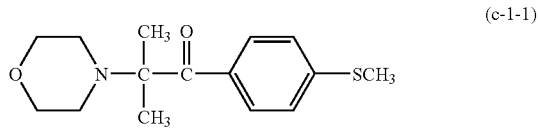

(c-1-1)

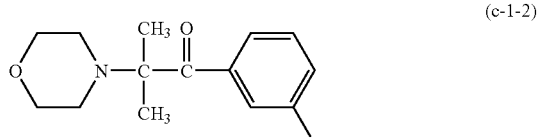

(c-1-2)

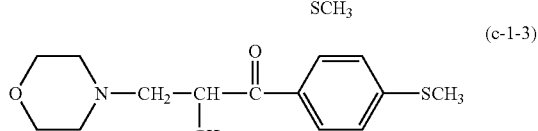

(c-1-3)

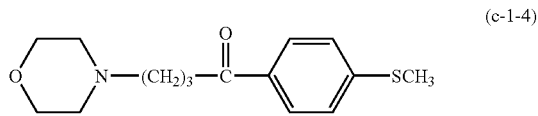

(c-1-4)

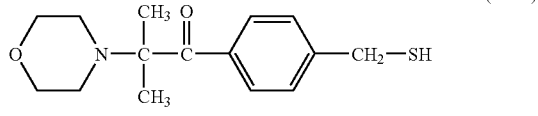

(c-1-5)

As the component (C), one type of component may be used alone, or two or more types may be used in combination.

The amount of the component (C) within the positive resist composition of the present invention is preferably from 0.01 to 5 parts by weight, more preferably from 0.1 to 3 parts by weight, and still more preferably from 0.1 to 1.5 parts by weight, relative to 100 parts by weight of the component (A). By making the amount of the component (C) at least as large as the lower limit of the above-mentioned range, the effects in suppressing footing of the resist pattern can be enhanced. On the other hand, by making the amount of the component (C) no more than the upper limit of the above-mentioned range, the sensitivity can be improved.

The component (C) is a compound known as a radical polymerization initiator, and commercially available compounds can be used. In general, polymerization initiators are components removed by purification after polymerization reaction, and are not typically present as components of resist compositions.

<Component (D)>

In the resist composition of the present invention, for improving the resist pattern shape and the post exposure stability of the latent image formed by the pattern-wise exposure of the resist layer, a nitrogen-containing organic compound (D) (hereafter referred to as the component (D)) other than the above-mentioned component (C) may be added.

A multitude of these components (D) have already been proposed, and any of these known compounds may be used, although a cyclic amine, an aliphatic amine, and particularly a secondary aliphatic amine or tertiary aliphatic amine is preferable. Here, an aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (namely, alkylamines or alkyl alcohol amines).

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Among these, trialkylamines of 5 to 10 carbon atoms are preferable, and tri-n-pentylamine and tri-n-octylamine are particularly preferable, and tri-n-pentylamine is most preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These compounds can be used either alone, or in combinations of two or more different compounds.

The component (D) is typically used in an amount within a range from 0.01 to 5.0 parts by weight, relative to 100 parts by weight of the component (A).

<Optional Components>

In the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added as an optional component.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition according to the third aspect of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These organic solvents can be used individually, or as a mixed solvent containing two or more different solvents.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration that enables application of a coating solution to a substrate, in accordance with the thickness of the coating film. In general, the organic solvent is used in an amount such that the solid content of the resist composition becomes within the range from 2 to 20% by weight, and preferably from 5 to 15% by weight.

By using the resist composition of the present invention, a resist pattern having a large exposure margin (EL margin) and excellent lithography properties can be formed. The reason for this has not been elucidated yet, but is presumed as follows.

In the resist composition of the present invention, the aforementioned component (B1) is used as an acid generator.

The anion moiety of the component (B1) has a structure in which a functional group having an aromatic organic group "$R^2-CH_2-O$" is introduced into the skeleton "$Y^1-SO_3-$". As a result, the anion moiety of the component (B1) has a three-dimensionally bulky structure, as compared to a fluorinated alkylsulfonic ion which has been conventionally used as an anion moiety. Therefore, even though the number of carbon atoms of the alkylene group for $Y^1$ which may be fluorinated is as small as 1 to 4, diffusion of the acid generated in the exposed regions to the unexposed regions can be suppressed, as compared to the anion moiety of a conventional acid generator such as nonafluorobutanesulfonate. As a result, it is presumed that the difference in alkali solubility between the exposed regions and the unexposed regions (i.e., dissolution contrast) can be improved, and consequently resist pattern shapes can also be improved. Further, it is thought that even if the exposure dose varies to some extent, the amount of acid sufficient to decompose the acid dissociable group within the structural unit (a1) is generated, thereby improving EL margin and forming resist patterns with excellent lithography properties.

Furthermore, while perfluoroalkyl chains of 6 to 10 carbon atoms exhibit poor solubility, the alkyl chain of the alkylene group of 1 to 4 carbon atoms for $Y^1$ which may be fluorinated is expected to be safer in terms of handling when the risk of bioaccumulation is taken into consideration.

The EL margin is the range of the exposure dose at which a resist pattern can be formed with a size within a predetermined range of variation from a target size, when exposure is conducted by changing the exposure dose, i.e., the range of the exposure dose at which a resist pattern faithful to the mask pattern can be formed. The larger the exposure margin, the smaller the variation in the pattern size depending on the change in the exposure dose, thereby resulting in favorable improvement in the process margin.

Furthermore, according to the resist composition of the present invention, mask reproducibility during formation of a resist pattern, for example, a mask error factor (MEF), a hole circularity and uniformity during formation of a hole pattern, line width roughness (LWR) during formation of a line pattern, and the like can be improved. The reason for these improvements has not been elucidated yet, but is presumed to be the same as the reason for causing the above-mentioned improvements in the EL margin. The MEF is a parameter that indicates how faithfully mask patterns of differing dimensions can be reproduced by using the same exposure dose with fixed pitch and changing the mask size (namely, the hole diameter in hole patterns and the line width in line and space patterns). LWR is a phenomenon in which the line width of the formed line pattern becomes heterogeneous, and improvement in the level of LWR becomes an important issue as pattern miniaturization progresses.

<<Method of Forming a Resist Pattern>>

Next, the method of forming a resist pattern according to the fourth aspect of the present invention will be described.

The method of forming a resist pattern according to the present invention includes: applying a resist composition of the third aspect of the present invention to a substrate to form a resist film on the substrate; conducting exposure of the resist film; and alkali-developing the resist film to form a resist pattern.

More specifically, the method for forming a resist pattern according to the present invention can be performed, for example, as follows.

Firstly, the above-mentioned resist composition is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, developing is conducted using an alkali developing solution such as a 0.1 to 10% by weight aqueous solution of tetramethylammonium hydroxide, preferably followed by rinsing with pure water, and drying. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be exemplified. Specific examples of the material of the substrate include a silicon wafer; metals such as copper, chromium, iron and aluminum; and glass. Suitable materials for the wiring pattern include copper, aluminum, nickel, and gold.

Further, as the substrate, any one of the above-exemplified substrates provided with an inorganic and/or organic film on the surface thereof may be used. As the inorganic film, an inorganic antireflection film (inorganic BARC) can be exemplified. As the organic film, an organic antireflection film (organic BARC) can be exemplified.

Further, the wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition according to the third aspect of the present invention is effective to KrF excimer laser, ArF excimer laser, EB and EUV, and particularly effective to ArF excimer laser.

EXAMPLES

As follows is a more detailed description of the present invention based on a series of examples, although the scope of the present invention is in no way limited by these examples.

Example 1

Synthesis of Compound (b-12-1)

[Chemical Formula 52]

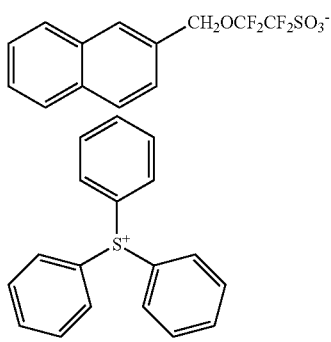

(b-12-1)

16.7 ml of tetrahydrofuran was added to 5.0 g of 2-naphthylmethyloxytetrafluoroethanesulfonylfluoride (1), and an aqueous solution obtained by dissolving 0.98 g of lithium hydroxide in 13.6 ml of pure water was dropwise added to the resulting solution in an ice bath. Then, the solution was stirred in the ice bath. As no absorption by —$SO_2F$ was observed at −217.6 ppm by $^{19}F$-NMR, it was confirmed that all fluorinated sulfonyl groups were converted to lithium sulfonate.

Thereafter, the reaction liquid was concentrated and dried to obtain a white viscous solid (crude product). The obtained crude product was dissolved in 14.2 ml of acetone, and filtered to remove the by-produced LiF. The filtrate was concentrated, thereby obtaining 5.50 g of a precursor compound (2).

[Chemical Formula 53]

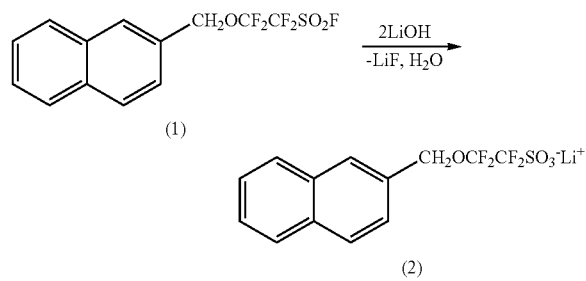

Subsequently, 6.99 g of triphenylsulfonium bromide was dissolved in 125 ml of pure water. 5.50 g of the precursor compound (2) was added to the resulting solution, and stirred at room temperature for 19 hours. Then, 125 g of dichloromethane was added thereto and stirred, and the organic phase was separated and taken out. The organic phase was washed with 40 ml of pure water, and the organic phase was separated and taken out. The extracted organic phase was concentrated and dried, thereby obtaining 7.09 g of the objective compound (3) (yield: 75.2%).

[Chemical Formula 54]

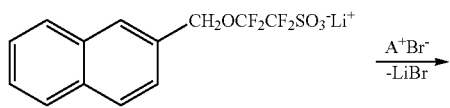

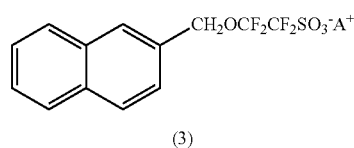

wherein $A^+$ is triphenylsulfonium.

The compound (3) was analyzed by NMR.

$^1H$-NMR (acetone-d6, 400 MHz): δ (ppm)=8.01-7.47 (m, 22H, $H^a$), 5.23 (s, 2H, $H^b$).

$^{19}F$-NMR (acetone-d6, 376 MHz): δ (ppm)=79.2, 111.8.

From the results shown above, it was confirmed that the compound had a structure shown below.

[Chemical Formula 55]

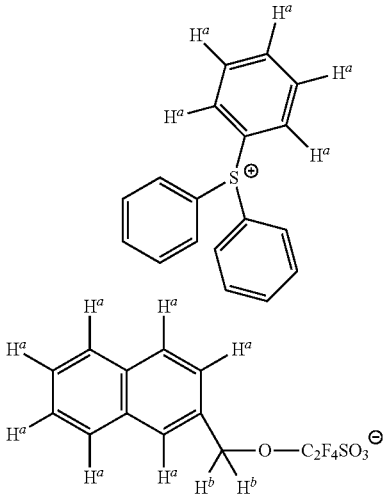

Example 2, Comparative Example 1

Synthesis of Polymer (A)-1

A copolymer (A)-1 was synthesized using a conventional dropwise polymerization method and copolymerizing the monomers represented by formulas (1) to (3) shown below at a molar ratio of 35:45:20. The weight average molecular weight (Mw) and dispersity (Mw/Mn) of the copolymer (A)-1 were 7,000 and 1.7, respectively. The Mw and Mw/Mn of the copolymer (A)-1 were determined by the polystyrene equivalent value as measured by gel permeation chromatography (GPC).

In formula (A)-1, the subscript numerals shown to the bottom right of the parentheses ( ) indicate the percentage (mol %) of the respective structural units within the copolymer. The compositional ratio was determined by $^{13}$C-NMR.

[Chemical Formula 56]

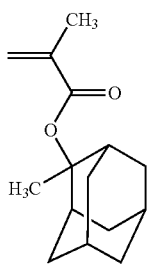
(1)

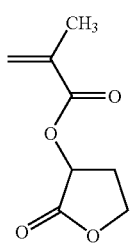
(2)

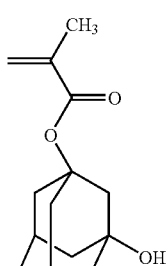
(3)

[Chemical Formula 57]

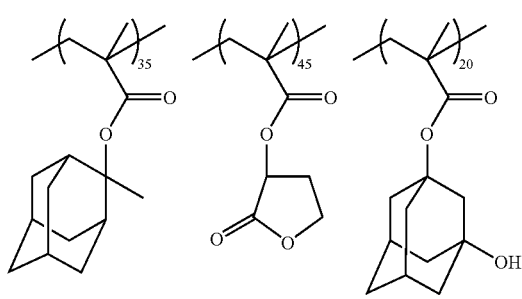
(A)-1

<Preparation of Positive Resist Composition Solution>

The components shown in Table 1 were mixed together and dissolved to obtain positive resist composition solutions.

TABLE 1

|  | Component (A) | Component (B) | Component (D) | Component (E) | Component (S) | |
|---|---|---|---|---|---|---|
| Example 2 | (A)-1 [100] | (B)-1 [4.32] | (D)-1 [0.54] | (E)-1 [1.34] | (S)-1 [2,380] | (S)-2 [10] |
| Comparative Example 1 | (A)-1 [100] | (B)-2 [4.00] | (D)-1 [0.54] | (E)-1 [1.34] | (S)-1 [2,380] | (S)-1 [10] |

In Table 1, the reference characters indicate the following. Further, the values in brackets [ ] indicate the amount (in terms of parts by weight) of the component added.

(A)-1: a copolymer represented by formula (A)-1 above.
(B)-1: an acid generator represented by chemical formula (b1-12-1) above (the compound of Example 1).
(B)-2: triphenylsulfonium heptafluoropropane sulfonate.
(D)-1: tri-n-pentylamine.
(E)-1: salicylic acid.
(S)-1: a mixed solvent of PGMEA/PGME=6/4 (weight ratio).
(S)-2: γ-butyrolactone.

The molar ratios of the aforementioned components (B)-1 and (B)-2 relative to the component (A) are the same.

<Evaluation of Lithography Properties>

Using the obtained positive resist composition solutions, resist patterns were formed, and the following lithography properties were evaluated.

[Resolution•Sensitivity]

An organic antireflection film composition (product name: ARC29A, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 77 nm. Then, the positive resist composition solution obtained above was applied onto the antireflection film using a spinner, and was then prebaked (PAB) on a hotplate at 120° C. for 60 seconds and dried, thereby forming a resist film having a film thickness of 120 nm.

Subsequently, the resist film was selectively irradiated with an ArF excimer laser (193 nm) through a mask pattern (6% half tone), using an ArF exposure apparatus NSR-S306 (manufactured by Nikon Corporation, NA (numerical aperture)=0.78, 2/3 annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was rinsed for 30 seconds with pure water, followed by drying by shaking, thereby forming a line and space (1:1) resist pattern (L/S pattern). In this manner, the optimum exposure dose (sensitivity: Eop, mJ/cm$^2$) for forming a L/S pattern having a line width of 90 nm and a pitch of 180 nm was determined. The results are shown in Table 2.

TABLE 2

|  | Example 2 | Comparative Example 1 |
|---|---|---|
| Eop (mJ/cm$^2$) | 61.5 | 35.0 |
| EL margin (%) | 9.1 | 5.4 |

[Evaluation of Exposure Margin (EL Margin)]

L/S patterns with a target dimension of a line width of 90 nm and a pitch of 180 nm were formed by changing the exposure dose.

The exposure dose with which a L/S (1:1) pattern having a dimension of the target dimension (90 nm)±5% (i.e., 85.5 to 94.5 nm) was determined, and the EL margin (unit: %) was determined by the following formula:

EL margin (%)=(|E1−E2|/Eop)×100 wherein E1 represents the exposure dose (mJ/cm$^2$) for forming a L/S pattern having a line width of 94.5 nm, and E2 represents the exposure dose (mJ/cm$^2$) for forming a L/S pattern having a line width of 85.5 nm.

The larger the value of EL margin, the smaller the fluctuation in the pattern size accompanied by the variation in the exposure dose. As a result, it was confirmed that the resist composition of Example 2 according to the present invention could achieve excellent lithography properties in terms of EL margin.

[Evaluation of Resist Pattern Shape]

With respect to the L/S patterns having a line width of 90 nm and a pitch of 180 nm that were obtained in Example 2 and Comparative Example 1, the cross-sectional shape of the resist patterns was observed using a scanning electron microscope (product name: S-4700; manufactured by Hitachi, Ltd.). As a result, it was confirmed that the resist pattern obtained in Example 2 exhibited a higher rectangularity compared to that of the resist pattern obtained in Comparative Example 1.

Examples 3 and 4

Preparation of Positive Resist Composition Solution

The components shown in Table 3 were mixed together and dissolved to obtain positive resist composition solutions.

TABLE 3

|  | Component (A) | Component (B) | Component (C) | Component (S) |
|---|---|---|---|---|
| Example 3 | (A)-1 [100] | (B)-1 [4.80] | (C)-1 [0.80] | (S)-1 [2,380] |
| Example 4 | (A)-1 [100] | (B)-1 [9.60] | (C)-1 [0.80] | (S)-1 [2,380] |

In Table 3, the reference characters indicate the following. Further, the values in brackets [ ] indicate the amount (in terms of parts by weight) of the component added.

(A)-1: a copolymer represented by formula (A)-1 above.
(B)-1: an acid generator represented by chemical formula (b1-12-1) above (the compound of Example 1).
(C)-1: a compound represented by chemical formula (c-1-1) shown below.

[Chemical Formula 58]

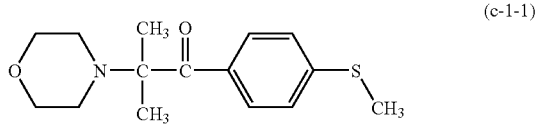

(c-1-1)

(S)-1: a mixed solvent of PGMEA/PGME=6/4 (weight ratio).

<Evaluation of Lithography Properties>

Using the obtained positive resist composition solutions, resist patterns were formed, and the following lithography properties were evaluated.

[Resolution•Sensitivity]

An organic antireflection film composition (product name: ARC29A, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 77 nm. Then, the positive resist composition solution obtained above was applied onto the antireflection film using a spinner, and was then prebaked (PAB) on a hotplate at 110° C. for 60 seconds and dried, thereby forming a resist film having a film thickness of 150 nm.

Subsequently, the resist film was selectively irradiated with an ArF excimer laser (193 nm) through a mask pattern (6% half tone), using an ArF exposure apparatus NSR-S302 (manufactured by Nikon Corporation, NA (numerical aperture)=0.60, 2/3 annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was rinsed for 30 seconds with pure water, followed by drying by shaking, thereby forming a line and space (1:1) resist pattern (L/S pattern). In this manner, the optimum exposure dose (sensitivity: Eop, mJ/cm$^2$) for forming a L/S pattern having a line width of 120 nm and a pitch of 240 nm was determined.

The results are shown in Table 4.

TABLE 4

|  | Example 3 | Example 4 |
|---|---|---|
| Eop (mJ/cm$^2$) | 42.5 | 19.0 |
| EL margin (%) | 7.1 | 8.0 |

[Evaluation of Exposure Margin (EL Margin)]

L/S patterns with a target dimension of a line width of 120 nm and a pitch of 240 nm were formed by changing the exposure dose.

The exposure dose with which a L/S (1:1) pattern having a dimension of the target dimension (120 nm)±5% (i.e., 114 to 126 nm) was determined, and the EL margin (unit: %) was determined by the following formula. The results are shown in Table 4.

EL margin (%)=(|E1−E2|/Eop)×100 wherein E1 represents the exposure dose (mJ/cm$^2$) for forming a L/S pattern having a line width of 126 nm, and E2 represents the exposure dose (mJ/cm$^2$) for forming a L/S pattern having a line width of 114 nm.

The larger the value of EL margin, the smaller the fluctuation in the pattern size accompanied by the variation in the exposure dose. As a result, it was confirmed that the resist compositions of Examples 3 and 4 according to the present invention could achieve excellent lithography properties in terms of EL margin.

[Evaluation of Resist Pattern Shape]

With respect to the L/S patterns having a line width of 120 nm and a pitch of 240 nm that were obtained in Examples 3 and 4, the cross-sectional shape of the resist patterns was observed using a scanning electron microscope (product name: S-4700; manufactured by Hitachi, Ltd.). As a result, it was confirmed that the resist patterns obtained in Examples 3 and 4 exhibited high rectangularity.

Example 5

Synthesis of Compound (b-12-25)

[Chemical Formula 59]

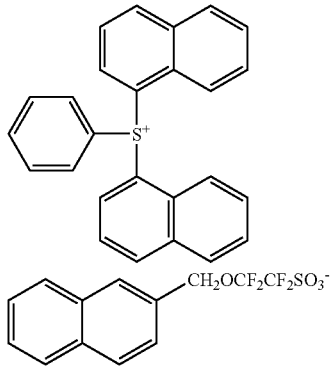

(b-12-25)

A compound (b-12-25) represented by formula (b-12-25) above was synthesized by the following procedures.

120 ml of tetrahydrofuran was added to 3.63 g of dinaphthylsulfoxide, and the resulting solution was cooled. 1.81 g of phenylmagnesium bromide was added to this solution, and the resulting solution was stirred at room temperature for 24 hours. 44.3 g of pure water was added to this solution, followed by washing with t-butylmethylether, and an aqueous phase was then collected by separation. 4.12 g of a 2-naphthylmethyloxytetrafluoroethanesulfonyl lithium salt and 41.2 g of dichloromethane were added to the obtained aqueous phase, and the resultant was stirred at room temperature. The resultant was washed with hydrochloric acid and pure water in this order, and was then concentrated, thereby obtaining 1.90 g of the objective compound (b-12-25) (yield: 27.2%).

The obtained compound (b-12-25) was analyzed by NMR. The results are shown below.

$^1$H-NMR (CDCl$_3$, 400 MHz): δ (ppm)=8.31 (d, 2H, H$^a$), 8.11 (d, 2H, H$^b$), 7.93 (d, 2H, H$^c$), 7.84-7.55 (m, 15H, H$^d$), 7.44 (m, 2H, H$^e$), 7.34 (m, 5H, H$^f$), 5.12 (s, 2H, H$^g$).

$^{19}$F-NMR (CDCl$_3$, 376 MHz): δ (ppm)=85.0, 117.1.

From the results shown above, it was confirmed that the obtained compound (b-12-25) had a structure shown below.

[Chemical Formula 60]

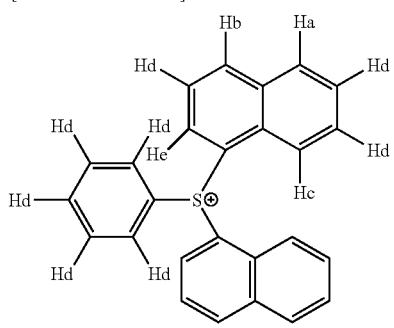

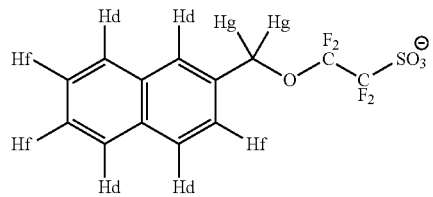

Example 6

Synthesis of Compound (b-12-3)

[Chemical Formula 61]

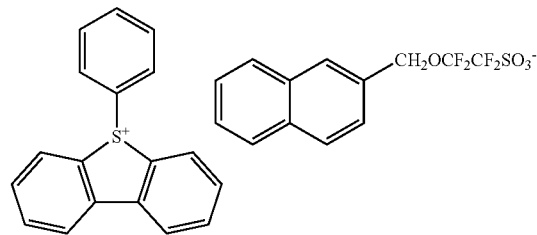

(b-12-3)

A compound (b-12-3) represented by formula (b-12-3) above was synthesized by the following procedures.

150 ml of tetrahydrofuran was added to 3.0 g of dibenzothiophene oxide, and the resulting solution was cooled. 2.26 g of phenylmagnesium bromide was added to this solution, and the resulting solution was stirred at room temperature for 24 hours. 42.6 g of pure water was added to this solution, followed by washing with t-butylmethylether, and an aqueous phase was then collected by separation. 5.15 g of a 2-naphthylmethyloxytetrafluoroethanesulfonyl lithium salt and 51.5 g of dichloromethane were added to the obtained aqueous phase, and the resultant was stirred at room temperature. The resultant was washed with hydrochloric acid and pure water in this order, and was then concentrated, thereby obtaining 2.30 g of the objective compound (b-12-3) (yield: 30.8%).

The compound (b-12-3) was analyzed by NMR. The results are shown below.

$^1$H-NMR (CDCl$_3$, 400 MHz): δ (ppm)=8.52 (d, 2H, H$^a$), 8.37 (d, 2H, H$^b$), 7.99-7.89 (m, 6H, H$^c$), 7.79-7.69 (m, 3H, H$^d$), 7.62 (m, 4H, H$^e$), 7.53 (m, 3H, H$^f$), 5.21 (s, 2H, H$^g$).

$^{19}$F-NMR (CDCl$_3$, 376 MHz): δ (ppm)=82.9, 115.9.

From the results shown above, it was confirmed that the compound had a structure shown below.

[Chemical Formula 62]

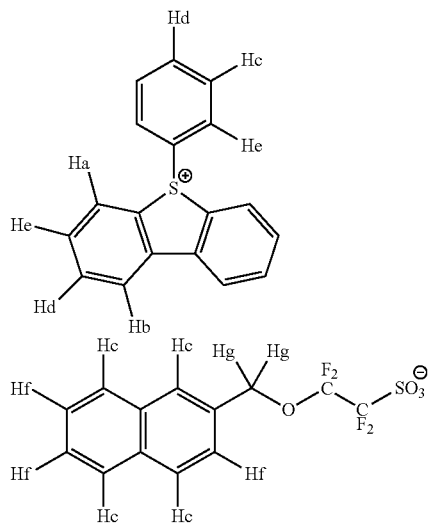

Examples 7 to 9 and Comparative Example 2

Preparation of Positive Resist Composition Solution

The components shown in Table 5 were mixed together and dissolved to obtain positive resist composition solutions.

TABLE 5

| | Component (A) | Component (B) | Component (D) | Component (E) | Component (S) | |
|---|---|---|---|---|---|---|
| Example 7 | (A)-1 [100] | (B)-1 [8.3] | (D)-1 [1.2] | (E)-1 [1.32] | (S)-1 [2,380] | (S)-2 [10] |
| Example 8 | (A)-1 [100] | (B)-3 [13.2] | (D)-1 [1.2] | (E)-1 [1.32] | (S)-1 [2,380] | (S)-2 [10] |
| Example 9 | (A)-1 [100] | (B)-4 [10.8] | (D)-1 [1.2] | (E)-1 [1.32] | (S)-1 [2,380] | (S)-2 [10] |
| Comparative Example 2 | (A)-1 [100] | (B)-5 [8.0] | (D)-1 [1.2] | (E)-1 [1.32] | (S)-1 [2,380] | (S)-2 [10] |

In Table 5, the reference characters indicate the following. Further, the values in brackets [ ] indicate the amount (in terms of parts by weight) of the component added.

The components (A)-1, (B)-1, (D)-1, (E)-1, (S)-1 and (S)-2 are the same as the components (A)-1, (B)-1, (D)-1, (E)-1, (S)-1 and (S)-2 shown in Table 1.

(B)-3: the compound (b-12-25) of Example 5.

(B)-4: the compound (b-12-3) of Example 6.

(B)-5: (4-methylphenyl)diphenylsulfonium nonafluorobutane sulfonate.

<Evaluation of Lithography Properties>

Using the obtained positive resist composition solutions, resist patterns were formed, and the following lithography properties were evaluated.

[Resolution•Sensitivity]

An organic antireflection film composition (product name: ARC29A, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 77 nm. Then, the positive resist composition solution obtained above was applied onto the antireflection film using a spinner, and was then prebaked (PAB) on a hotplate at 110° C. for 60 seconds and dried, thereby forming a resist film having a film thickness of 120 nm.

Subsequently, the resist film was selectively irradiated with an ArF excimer laser (193 nm) through a mask pattern (6% half tone), using an ArF exposure apparatus NSR-S306 (manufactured by Nikon Corporation, NA (numerical aperture)=0.78, 2/3 annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was rinsed with pure water for 30 seconds, followed by drying by shaking.

As a result, a L/S pattern with a line width of 80 nm and a pitch of 160 nm was formed in all the examples using any of the positive resist compositions.

The optimum exposure dose (sensitivity: Eop, mJ/cm$^2$) for forming a L/S pattern having a line width of 80 nm and a pitch of 160 nm was determined. The results are shown in Table 6.

[Evaluation of Line Width Roughness (LWR)]

With respect to each of the L/S patterns formed with the above-mentioned Eop, 5 points in the lengthwise direction of the line were measured using a measuring SEM (product name: S-9220, manufactured by Hitachi, Ltd.; acceleration voltage: 800V), and from the results, the value of 3 times the standard deviation s (i.e., 3s) (unit: nm) was calculated as a yardstick of LWR. The results are shown in Table 6.

The smaller this 3s value is, the lower the level of roughness of the line width, indicating that a line with a uniform width was obtained.

TABLE 6

| | Example 7 | Example 8 | Example 9 | Comparative Example 2 |
|---|---|---|---|---|
| Eop (mJ/cm$^2$) | 48.0 | 96.0 | 136.5 | 45.0 |
| LWR (nm) | 9.5 | 7.1 | 9.1 | 13.3 |

As seen from the results shown above, the L/S patterns formed in Examples 7 to 9 according to the present invention exhibited a higher degree of uniformity in each line width and had excellent shape, as compared to that formed in Comparative Example 2.

Example 10

Synthesis of Compound (b-12-31)

5.81 g of 4-methylphenyldiphenylsulfonium bromide was dissolved in 29.0 g of pure water, followed by the addition of 58.1 g of dichloromethane and 6.7 g of a 2-naphthylmethyloxytetrafluoroethanesulfonyl lithium salt thereto, and the resultant was stirred at room temperature for 14 hours.

Thereafter, the dichloromethane phase was separated, and washed with diluted hydrochloric acid, ammonia and water in this order. Then, the dichloromethane phase was reprecipitated using n-hexane (388.4 g), thereby obtaining 8.7 g of the objective compound (b-12-31) in the form of a white solid.

[Chemical Formula 63]

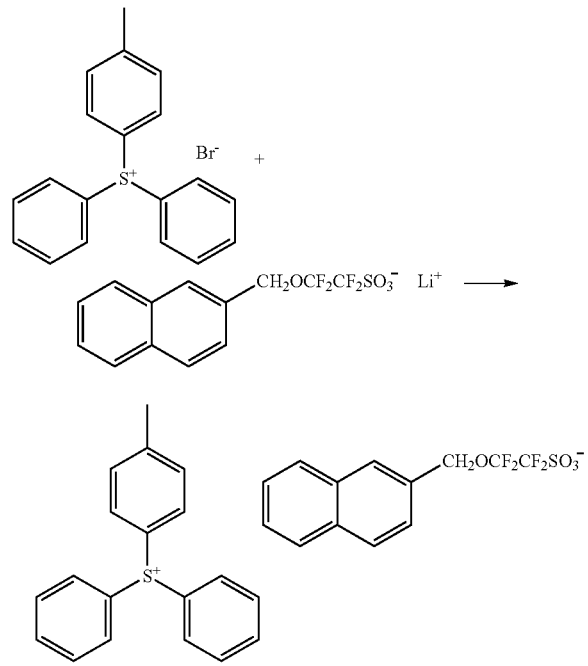

The compound (b-12-31) was analyzed by NMR. The results are shown below.

$^1$H-NMR (DMSO-d6, 400 MHz): δ (ppm)=7.51-7.96 (m, Ar+Naph, 21H), 5.20 (s, CH$_2$, 2H), 2.42 (s, CH$_3$, 3H).

$^{19}$F-NMR (DMSO-d6, 376 MHz): δ (ppm)=−80.5, 113.7.

From the results shown above, it was confirmed that the compound had a structure shown above.

Examples 11 to 14 and Comparative Example 3

Preparation of Positive Resist Composition Solution

The components shown in Table 7 were mixed together and dissolved to obtain positive resist composition solutions.

<Evaluation of Lithography Properties>

Using the obtained positive resist composition solutions, resist patterns were formed, and the following lithography properties were evaluated.

[Resolution•Sensitivity]

An organic antireflection film composition (product name: ARC29A, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 77 nm. Then, the positive resist composition solution obtained above was applied onto the antireflection film using a spinner, and was then prebaked (PAB) on a hotplate at 110° C. for 60 seconds and dried, thereby forming a resist film having a film thickness of 120 nm.

Subsequently, the resist film was selectively irradiated with an ArF excimer laser (193 nm) through a mask pattern (6% half tone), using an ArF exposure apparatus NSR-S306 (manufactured by Nikon Corporation, NA (numerical aperture)=0.78, 2/3 annular illumination). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist film was rinsed with pure water for 30 seconds, followed by drying by shaking.

As a result, a L/S pattern with a line width of 80 nm and a pitch of 160 nm was formed in all the examples using any of the positive resist compositions.

The optimum exposure dose (sensitivity: Eop, mJ/cm$^2$) for forming a L/S pattern having a line width of 80 nm and a pitch of 160 nm was determined. The results are shown in Table 8.

[Evaluation of Mask Error Factor (MEF)]

When the L/S patterns were formed with the above-mentioned Eop using a mask pattern targeting a line width of 85 nm and a pitch of 180 nm, a mask pattern targeting a line width of 90 nm and a pitch of 180 nm and a mask pattern targeting a line width of 95 nm and a pitch of 180 nm, the MEF value was calculated as the slope of a straight line obtained by plotting the mask size on the horizontal axis and the formed pattern size on the vertical axis.

TABLE 7

|  | Component (A) | Component (B) | Component (D) | Component (E) | Component (S) | |
| --- | --- | --- | --- | --- | --- | --- |
| Example 11 | (A)-1 | (B)-1 | (D)-1 | (E)-1 | (S)-1 | (S)-2 |
|  | [100] | [8.3] | [0.9] | [1.32] | [2,380] | [10] |
| Example 12 | (A)-1 | (B)-3 | (D)-1 | (E)-1 | (S)-1 | (S)-2 |
|  | [100] | [9.7] | [0.5] | [1.32] | [2,380] | [10] |
| Example 13 | (A)-1 | (B)-3 | (D)-1 | (E)-1 | (S)-1 | (S)-2 |
|  | [100] | [19.4] | [1.0] | [1.32] | [2,380] | [10] |
| Example 14 | (A)-1 | (B)-6 | (D)-1 | (E)-1 | (S)-1 | (S)-2 |
|  | [100] | [8.7] | [0.9] | [1.32] | [2,380] | [10] |
| Comparative Example 3 | (A)-1 | (B)-5 | (D)-1 | (E)-1 | (S)-1 | (S)-2 |
|  | [100] | [8.0] | [1.2] | [1.32] | [2,380] | [10] |

In Table 7, (B)-6 is the compound (b-12-31) obtained in Example 10, and other reference characters are the same as the reference characters in Table 5. Further, the values in brackets [ ] indicate the amount (in terms of parts by weight) of the component added.

Furthermore, 8.3 parts by weight of (B)-1, 9.7 parts by weight of (B)-3, 8.0 parts by weight of (B)-5 and 8.7 parts by weight of (B)-6 are equimolar amounts.

[Evaluation of Line Width Roughness (LWR)]

With respect to each of the L/S patterns formed with the above-mentioned Eop, 5 points in the lengthwise direction of the line were measured using a measuring SEM (product name: S-9220, manufactured by Hitachi, Ltd.; acceleration voltage: 800V), and from the results, the value of 3 times the standard deviation s (i.e., 3s) (unit: nm) was calculated as a yardstick of LWR. The results are shown in Table 8.

TABLE 8

|  | Example 11 | Example 12 | Example 13 | Example 14 | Comparative Example 3 |
|---|---|---|---|---|---|
| Eop (mJ/cm$^2$) | 41.5 | 95.0 | 60.0 | 43.0 | 46.8 |
| MEF | 2.72 | 2.99 | 2.85 | 2.75 | 3.15 |
| LWR (nm) | 15.1 | 12.5 | 8.8 | 14.0 | 14.1 |

As seen from the results shown above, the L/S patterns formed in Examples 11 to 14 according to the present invention exhibited satisfactory MEF values, as compared to that formed in Comparative Example 3. Further, the levels of LWR achieved in these Examples were also the same as or higher than the level of LWR achieved in Comparative Example 3.

Example 15

Synthesis of Compound (b-12-13)

[Chemical Formula 64]

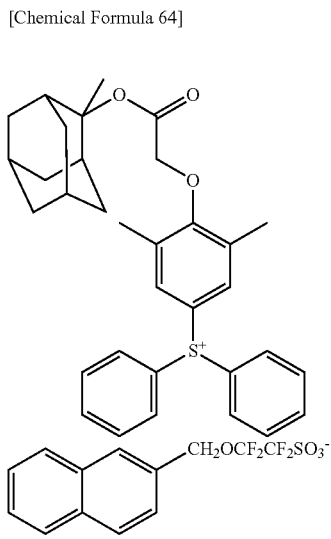

(b-12-13)

A compound (b-12-13) represented by formula (b-12-13) above was synthesized by the following procedures.

To methanesulfonic acid (60.75 g) at 20° C. or lower was added phosphorus oxide (8.53 g), 2,5-dimethylphenol (8.81 g) and diphenylsulfoxide (12.2 g) little by little. The resultant was left to stand for 30 minutes while maintaining the temperature at 15 to 20° C., followed by elevating the temperature to 40° C. and then left to stand for 2 hours. Then, the reaction liquid was dropwise added to pure water (109.35 g) cooled to 15° C. or lower. Thereafter, dichloromethane (54.68 g) was added and stirred, and the dichloromethane phase was collected. Hexane (386.86 g) at a temperature of 20 to 25° C. was charged into a separate vessel, and the dichloromethane phase was dropwise added thereto. Then, the resultant was left to stand at 20 to 25° C. for 30 minutes, followed by filtration, thereby obtaining 17.14 g of an objective compound (precursor compound (4-1)) (yield: 70.9%).

The obtained precursor compound (4-1) was analyzed by $^1$H-NMR. The results are shown below.

$^1$H-NMR (DMSO-d6, 600 MHz): δ (ppm)=7.61-7.72 (m, 10H, phenyl), 7.14 (s, 2H, H$^c$), 3.12 (s, 3H, H$^b$), 2.22 (s, 6H, H$^a$).

From the results shown above, it was confirmed that the precursor compound (4-1) had a structure shown below.

[Chemical Formula 65]

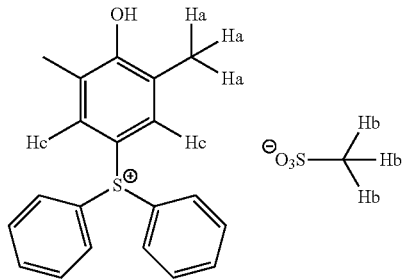

Subsequently, 4 g of the precursor compound (4-1) was dissolved in dichloromethane (79.8 g).

After confirming that the precursor compound (4-1) had dissolved, potassium carbonate (6.87 g) was added thereto, and 2-methyl-2-adamantane bromoacetate (3.42 g) was further added. A reaction was carried out under reflux for 24 hours, followed by filtration, washing with water, and crystallization with hexane. The resulting powder was dried under reduced pressure, thereby obtaining 3.98 g of an objective compound (precursor compound (4-2)) (yield: 66%).

The obtained precursor compound (4-2) was analyzed by $^1$H-NMR. The results are shown below.

$^1$H-NMR (CDCl$_3$, 400 MHz): δ (ppm)=7.83-7.86 (m, 4H, Phenyl), 7.69-7.78 (m, 6H, Phenyl), 7.51 (s, 2H, H$^d$), 4.46 (s, 2H, H$^c$), 2.39 (s, 6H, H$^a$), 2.33 (s, 2H, Adamantane), 2.17 (s, 2H, Adamantane), 1.71-1.98 (m, 11H, Adamantane), 1.68 (s, 3H, H$^b$), 1.57-1.61 (m, 2H, Adamantane).

From the results shown above, it was confirmed that the precursor compound (4-2) had a structure shown below.

[Chemical Formula 66]

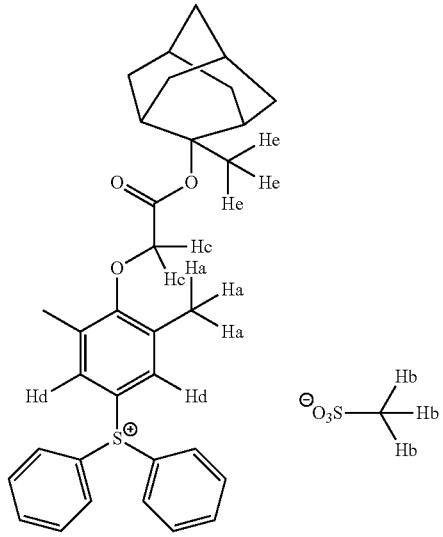

Subsequently, the precursor compound (4-2) (2.00 g) was dissolved in a mixed solution of water (10.00 g) and dichloromethane (10.00 g). Then, the precursor compound (2) of Example 1 (1.25 g) was added to the solution in small amounts, and the resultant was stirred at 25° C. for 1 hour. After the completion of the reaction, the dichloromethane solution was washed with water, and concentrated and solidified. The resulting powder was dispersed in hexane for washing, and the resultant was dried under reduced pressure, thereby obtaining 2.35 g of the objective compound (b-12-13) (yield: 84.2%).

The compound (b-12-13) was analyzed by NMR. The results are shown below.

$^1$H-NMR (CDCl$_3$, 400 MHz): δ (ppm)=7.84 (s, 1H, H$^f$), 7.71-7.77 (m, 3H, Phenyl+Naphthyl), 7.57-7.67 (m, 10H, Phenyl+Naphthyl), 7.39-7.51 (m, 3H, Phenyl+Naphthyl), 7.36 (s, 2H, H$^d$), 5.19 (s, 2H, H$^c$), 4.38 (s, 2H, H$^b$), 2.32 (s, 6H, H$^a$), 1.69-1.97 (m, 11H, Adamantane), 1.66 (s, 3H, H$^e$), 1.55-1.58 (d, 3H, Adamantane).

$^{19}$F-NMR (CDCl$_3$, 400 MHz): δ (ppm)=−76.87, −109.14.

From the results shown above, it was confirmed that the compound (b-12-13) had a structure shown below.

[Chemical Formula 67]

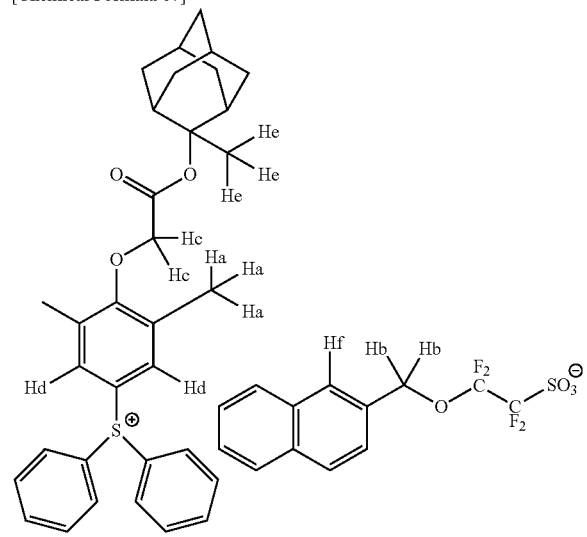

Example 16

Synthesis of Compound (b-12-19)

[Chemical Formula 68]

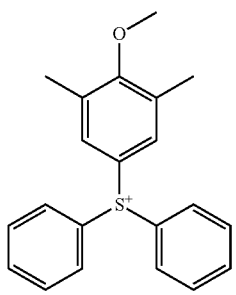
(b-12-19)

-continued

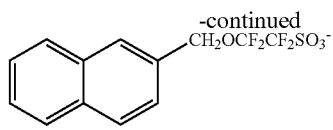

A compound (b-12-19) represented by formula (b-12-19) above was synthesized by the following procedures.

To methanesulfonic acid (25.00 g) controlled to 20° C. or lower was added phosphorus oxide (3.51 g), 2,5-dimethylanisole (4.04 g) and diphenylsulfoxide (5.00 g) little by little. The resultant was left to stand for 30 minutes while maintaining the temperature at 15 to 20° C., followed by leaving at room temperature for 15 hours. Then, the reaction liquid was dropwise added to pure water (45 g) cooled to 15° C. or lower. Thereafter, dichloromethane (22.5 g) was added and stirred, and the dichloromethane phase was collected. Then the dichloromethane phase was crystallized with hexane, thereby obtaining 6.53 g of an objective compound (precursor compound (5-1)) (yield: 63.5%).

The obtained precursor compound (5-1) was analyzed by $^1$H-NMR. The results are shown below.

$^1$H-NMR (DMSO-d6, 600 MHz): δ (ppm)=7.77-7.88 (m, 10H, phenyl), 7.62 (s, 2H, H$^c$), 3.78 (s, 3H, H$^d$), 2.40 (s, 3H, H$^b$), 2.33 (s, 6H, H$^d$).

From the results shown above, it was confirmed that the precursor compound (5-1) had a structure shown below.

[Chemical Formula 69]

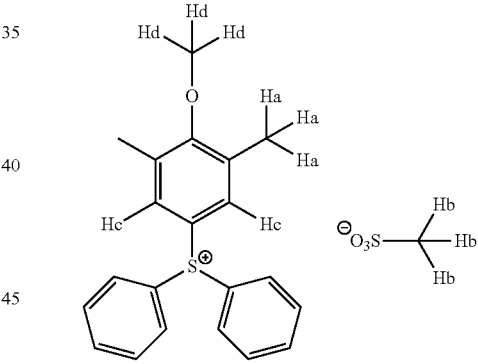

Subsequently, the precursor compound (5-1) (2.53 g) was dissolved in a mixed solution of water (12.64 g) and dichloromethane (12.0 g). Then, the precursor compound (2) obtained in Example 1 (2.19 g) was added to the solution little by little, and the resultant was stirred at 25° C. for 1 hour. After the completion of the reaction, the dichloromethane solution was washed with water, followed by crystallization with hexane, thereby obtaining 4.11 g of an objective compound (b-12-19) (yield: 90.0%).

The compound (b-12-19) was analyzed by $^1$H-NMR. The results are shown below.

$^1$H-NMR (CDCl$_3$, 400 MHz): δ (ppm)=7.83 (s, 1H, H$^e$), 7.37-7.80 (m, 16H, Phenyl+Naphthyl), 7.34 (s, 2H, H$^d$), 5.23 (s, 2H, H$^b$), 3.72 (s, 2H, H$^c$), 2.27 (s, 6H, H$^a$).

$^{19}$F-NMR (CDCl$_3$, 400 MHz): δ (ppm)=−79.6, −111.9.

From the results shown above, it was confirmed that the compound (b-12-19) had a structure shown below.

[Chemical Formula 70]

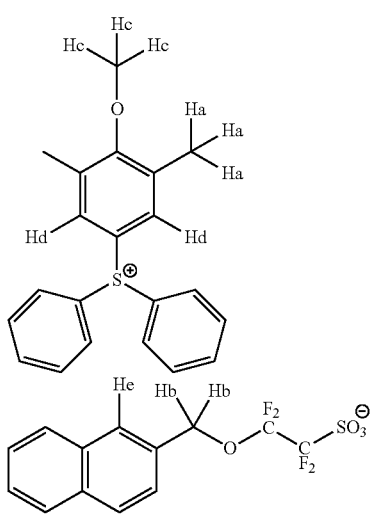

Examples 17 and 18, Comparative Example 4

Synthesis of Polymer (A)-2

A copolymer (A)-2 represented by formula (A)-2 shown below was synthesized using a conventional dropwise polymerization method and copolymerizing the monomers represented by formulas (4) to (6) shown below. The weight average molecular weight (Mw) and dispersity (Mw/Mn) of the copolymer (A)-2 were 7,000 and 2.0, respectively. The Mw and Mw/Mn of the copolymer (A)-2 were determined by the polystyrene equivalent value as measured by GPC.

In formula (A)-2, the subscript numerals shown at the bottom right of the parentheses ( ) indicate the percentage (mol %) of the respective structural units within the copolymer. The compositional ratio was determined by $^{13}$C-NMR.

[Chemical Formula 71]

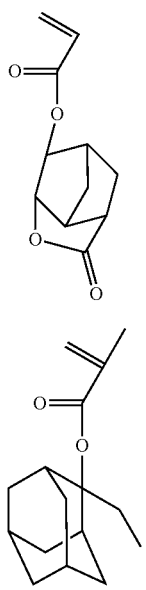

(4)

(5)

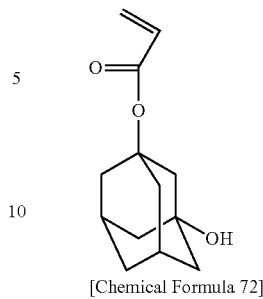

(6)

[Chemical Formula 72]

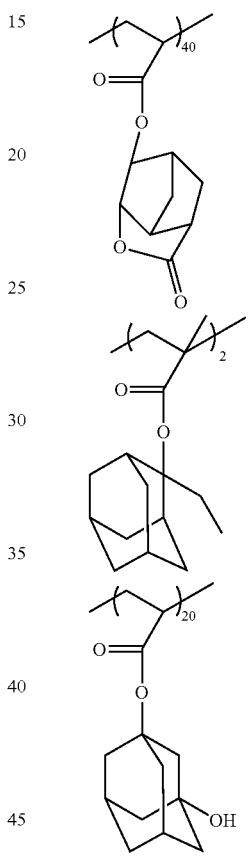

(A)-2

<Preparation of Positive Resist Composition Solution>

The components shown in Table 9 were mixed together and dissolved to obtain positive resist composition solutions.

TABLE 9

| | Component (A) | Component (B) | Component (D) | Component (S) |
|---|---|---|---|---|
| Example 17 | (A)-2 [100] | (B)-7 [6.90] | (D)-1 [0.10] | (S)-1 [2,380] |
| Example 18 | (A)-2 [100] | (B)-8 [5.34] | (D)-1 [0.10] | (S)-1 [2,380] |
| Comparative Example 4 | (A)-2 [100] | (B)-2 [4.94] | (D)-1 [0.10] | (S)-1 [2,380] |

In Table 9, the reference characters indicate the following. Further, the values in brackets [ ] indicate the amount (in terms of parts by weight) of the component added.

(A)-2: a copolymer (A)-2 represented by formula (A)-2 above.

(B)-7: the compound (b-12-13) of Example 15.
(B)-8: the compound (b-12-19) of Example 16.
The components (B)-2, (D)-1 and (S)-1 are the same as the components (B)-2, (D)-1 and (S)-1 shown in Table 1.
Furthermore, 6.90 parts by weight of (B)-7, 5.34 parts by weight of (B)-8 and 4.94 parts by weight of (B)-2 are equimolar amounts.

<Evaluation of Lithography Properties>

Using the obtained positive resist composition solutions, resist patterns were formed, and the following lithography properties were evaluated.

[Resolution•Sensitivity]

An organic antireflection film composition (product name: ARC29A, manufactured by Brewer Science Ltd.) was applied onto an 8-inch silicon wafer using a spinner, and the composition was then baked and dried on a hotplate at 205° C. for 60 seconds, thereby forming an organic antireflection film having a film thickness of 89 nm. Then, the positive resist composition solution obtained above was applied onto the antireflection film using a spinner, and was then prebaked (PAB) on a hotplate at 100° C. for 60 seconds and dried, thereby forming a resist film having a film thickness of 120 nm.

Subsequently, a coating solution for forming a protection film (product name: TSRC-002; manufactured by Tokyo Ohka Kogyo Co., Ltd.) was applied onto the resist film using a spinner, and then heated at 90° C. for 60 seconds, thereby forming a top coat with a film thickness of 28 nm.

Thereafter, using an ArF exposure apparatus for immersion lithography (product name: NSR-S609B, manufactured by Nikon Corporation, NA (numerical aperture)=1.07, 2/3 annular illumination, reduction ratio: 1/4, immersion medium: water), the resist film having a top coat formed thereon was selectively irradiated with an ArF excimer laser (193 nm) through a mask having a hole pattern (namely, through a mask in which holes with a hole diameter (CD) of 75 nm were arranged with equal spacing (pitch: 131 nm)).

Next, the top coat was removed using a protection-film removing solution (product name: TS-Remover-S; manufactured by Tokyo Ohka Kogyo Co., Ltd.). Then, a post exposure bake (PEB) treatment was conducted at 95° C. for 60 seconds, followed by development for 60 seconds at 23° C. in a 2.38% by weight aqueous solution of TMAH (product name: NMD-W; manufactured by Tokyo Ohka Kogyo Co., Ltd.). Then, the resist film was rinsed for 30 seconds with pure water, followed by drying by shaking.

As a result, in each of the examples, a hole pattern in which holes with a hole diameter (CD) of 70 nm were arranged with equal spacing (pitch: 131 nm) was formed on the resist film.

The optimum exposure dose Eop (mJ/cm$^2$) with which a hole pattern having a CD of 70 nm and a pitch of 131 nm was formed was determined. The results are shown in Table 10.

[Evaluation of Circularity]

Each of the hole patterns formed with the above-mentioned Eop was observed from the upper side thereof using a measuring SEM (product name: S-9220, manufactured by Hitachi, Ltd.), and with respect to 25 holes in each hole pattern, the distance from the center of the hole to the outer periphery thereof was measured in 24 directions. From the results, the value of 3 times the standard deviation σ (i.e., 3σ) was determined. The results are shown in Table 10.

The smaller this 3σ value is, the higher the level of circularity of the holes.

[Evaluation of CD Uniformity (CDU)]

With respect to each of the hole patterns formed with the above-mentioned Eop, the hole diameters (CD) of 25 holes were measured, and from the results, the value of 3 times the standard deviation σ (i.e., 3σ) was determined. The results are shown in Table 10.

The smaller this 3σ value is, the higher the level of CDU of the holes formed in the resist film.

TABLE 10

|  | Example 17 | Example 18 | Comparative Example 4 |
| --- | --- | --- | --- |
| Eop (mJ/cm$^2$) | 57.0 | 67.0 | 24.0 |
| Circularity | 4.09 | 3.49 | 4.34 |
| CDU | 11.99 | 12.04 | 14.48 |

From the results shown above, it was confirmed that the hole patterns formed in Examples 17 and 18 according to the present invention exhibited higher levels of circularity of each hole, and also higher levels of CD uniformity, as compared to the hole pattern formed in Comparative Example 4.

The invention claimed is:

1. A compound represented by general formula (b1-12) shown below:

$$R^2-CH_2-O-Y^1-SO_3^-A^+ \quad (b1\text{-}12)$$

wherein R$^2$ represents a monovalent aromatic organic group containing 10 to 20 carbon atoms; Y$^1$ represents an alkylene group of 1 to 4 carbon atoms which may be fluorinated; and A$^+$ represents a cation.

2. An acid generator comprising a compound of claim 1.

3. A resist composition comprising:
a base component (A) which exhibits changed solubility in an alkali developing solution under action of acid; and
an acid-generator component (B) which generates acid upon exposure,
wherein said acid-generator component (B) comprises an acid generator (B1) including a compound represented by general formula (b1-12) shown below:

$$R^2-CH_2-O-Y^1-SO_3^-A^+ \quad (b1\text{-}12)$$

wherein R$^2$ represents a monovalent aromatic organic group containing 10 to 20 carbon atoms; Y$^1$ represents an alkylene group of 1 to 4 carbon atoms which may be fluorinated; and A$^+$ represents a cation.

4. The resist composition according to claim 3,
wherein said base component (A) is a base component which exhibits increased solubility in an alkali developing solution under action of acid.

5. The resist composition according to claim 4,
wherein said base component (A) is a resin component (A1), and
includes a structural unit (a1) derived from an acrylate ester containing an acid dissociable, dissolution inhibiting group.

6. The resist composition according to claim 5,
wherein said base component (A) further includes a structural unit (a2) derived from an acrylate ester having a lactone-containing cyclic group.

7. The resist composition according to claim 5,
wherein said base component (A) further includes a structural unit (a3) derived from an acrylate ester having a polar group-containing aliphatic hydrocarbon group.

8. The resist composition according to claim 3, which further comprises a nitrogen-containing organic compound (D).

9. A method of forming a resist pattern, comprising:
applying a resist composition of claim 3 to a substrate to form a resist film on the substrate;
conducting exposure of said resist film; and
alkali-developing said resist film to form a resist pattern.

* * * * *